United States Patent [19]

Voroteliak et al.

[11] Patent Number: 5,783,396
[45] Date of Patent: Jul. 21, 1998

[54] METHOD OF DETECTING RUPTURE OF THE AMNIOTIC MEMBRANES IN PREGNANT MAMMALS

[76] Inventors: Victor Voroteliak, 342 Lillian Avenue, Salisbury, Queensland, 4107, Australia; David Michael Cowley, 16 Mapleleaf Street, Eight, Mile Plains, Brisbane, Queensland 4113, Australia

[21] Appl. No.: 513,902

[22] PCT Filed: Mar. 23, 1994

[86] PCT No.: PCT/AU94/00144

§ 371 Date: Sep. 7, 1995

§ 102(e) Date: Sep. 7, 1995

[87] PCT Pub. No.: WO94/21687

PCT Pub. Date: Sep. 29, 1994

[30] Foreign Application Priority Data

Mar. 23, 1993 [AU] Australia .................. PL7945

[51] Int. Cl.$^6$ .................. G01N 33/53; A61K 39/00; C07K 16/00; C07K 14/00
[52] U.S. Cl. .................. 435/7.1; 424/184.1; 435/4; 435/7.91; 435/7.92; 530/350; 530/387.1; 530/388.1; 530/412; 530/416; 530/417; 530/806; 530/851
[58] Field of Search .................. 424/184.1; 435/4, 435/7.1, 7.72, 7.9, 7.92, 7.93; 530/350, 387.1, 388.1, 412, 416, 417, 806, 851, 864

[56] References Cited

U.S. PATENT DOCUMENTS 5,281,522 1/1994 Sentei et al. .................. 435/7.9
5,514,598 5/1996 Doody .................. 436/518
5,554,504 9/1996 Rutanen .................. 435/7.8

FOREIGN PATENT DOCUMENTS 7059187 9/1988 Australia.
2517788 6/1989 Australia.
9132191 7/1992 Australia.

OTHER PUBLICATIONS

Lelle, Ralph J. et al. "Measurement of CEA, TPA, Neopterin, CA125, CA153 and CA199 in Sera of Pregnant Women, Umbilical Cord Blood and Amniotic Fluid" Gynecol Obstet Invest vol. 27 (issued 1989) (S Karger AG, Basel) see p. 137 to 142.

Primary Examiner—Ponnathapura Achutamurthy
Attorney, Agent, or Firm—Cushman Darby & Cushman IP Group of Pillsbury Madison & Sutro

[57] ABSTRACT

The present invention relates to the method of detecting rupture of the amniotic membranes in pregnant mammals including humans using an immunoassay and reagents useful in such an assay. The method describes how to prepare a suitable protein antigen from amniotic fluid, gives criteria for the selection of this protein from the mixture of proteins present in amniotic fluid using the techniques of protein purification, gives criteria for assessing a sufficient degree of antigen purity for raising antibodies to the antigen and shows how the resultant antibodies can be used in immunoassays to detect the presence of amniotic fluid in the vagina and consequently to detect rupture of the amniotic membranes. The method also relates to the detection of amniotic fluid in other situations.

12 Claims, 25 Drawing Sheets

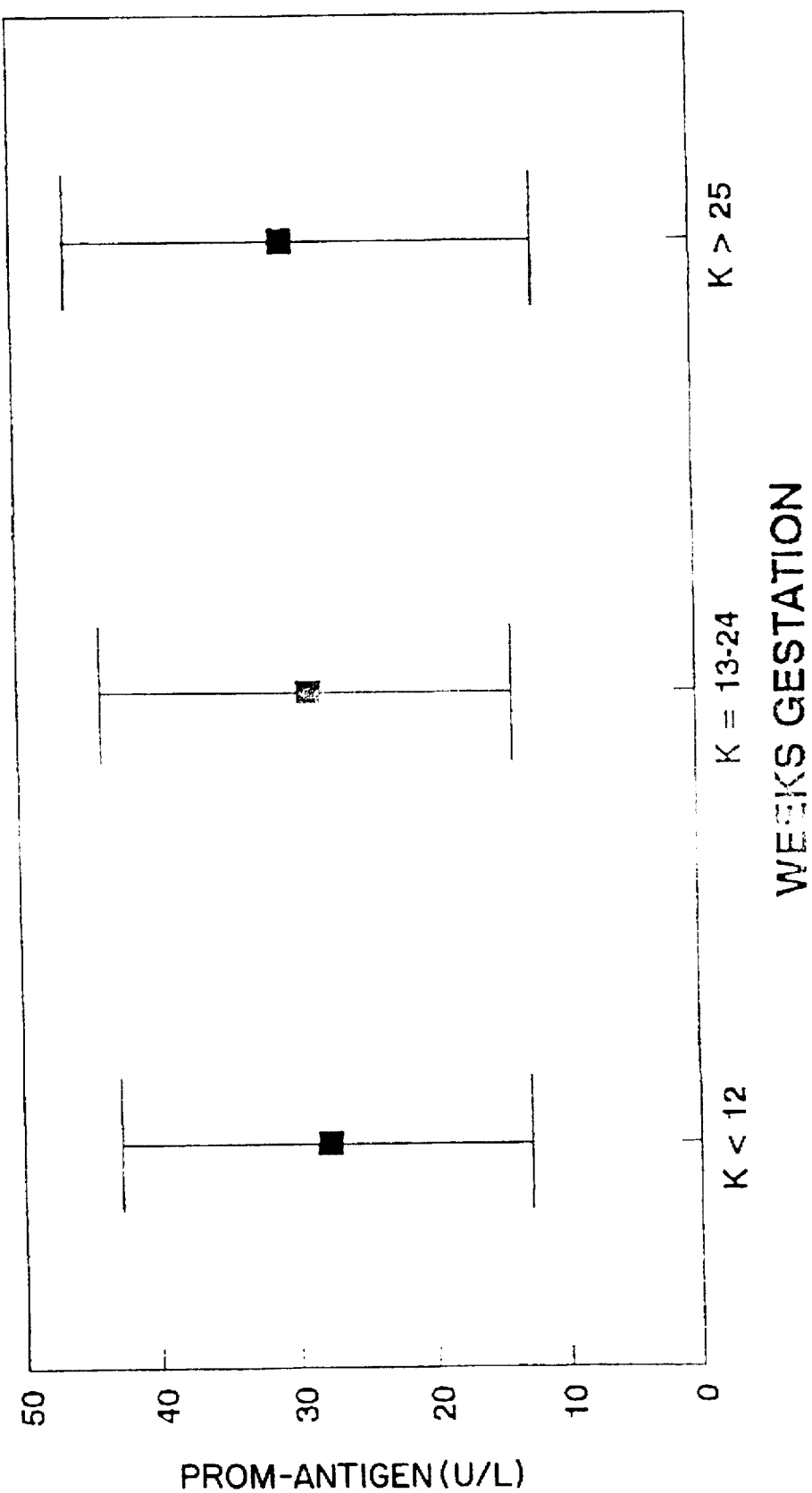

METHOD OF DETECTING RUPTURE OF THE AMNIOTIC MEMBRANES IN PREGNANT MAMMALS

FIELD OF THE INVENTION

The present invention relates to the method of detecting rupture of the amniotic membranes in pregnant mammals including humans using an immunoassay and reagents useful in such an assay. The method describes how to prepare a suitable protein antigen from amniotic fluid, gives criteria for the selection of this protein from the mixture of proteins present in amniotic fluid using the techniques of protein purification, gives criteria for assessing a sufficient degree of antigen purity for raising antibodies to the antigen and shows how the resultant antibodies can be used in immunoassays to detect the presence of amniotic fluid in the vagina and consequently to detect rupture of the amniotic membranes. The method also relates to the detection of amniotic fluid in other situations.

BACKGROUND OF THE INVENTION (1) Rupture of the amniotic membranes in mammals.
(2) Detection of rupture of the amniotic membranes in mammals.
(3) Proteins present in amniotic fluid.

1. RUPTURE OF THE AMNIOTIC MEMBRANES IN MAMMALS

Premature rupture of the fetal membranes was observed in 14–16% of all pregnancies (Polansky, G. H., et al., J. Reprod. Med. 30:189 (1985); Trap, P., et al., Gynecol. Obstet. Invest. 28:14 (1989)), while another study found the rupture of fetal membranes in 3–14% of all pregnancies was not followed by labour (Larsen, L., Br. Med. J. 1:1165 (1979). On rupture of the membranes, Duff (Obstet. Gynecol. 63:697 (1984)) observed that spontaneous labour followed within 24 hours in 80% of patients, with 10% remaining undelivered after a period of 48 hours. The perinatal mortality doubles after a latent period of 24 hours and again after 48 hours (Overstreet & Romney, Am. J. Obstet. Gynaecol. 90:1036 (1966)). Delayed onset of labour carries with it an increased risk of maternal and perinatal infection and mortality (Kapeller-Adler, R. et al., Biochim. Biophys. Acta. 67:542–565 (1963); Overstreet, above). Therefore the accurate detection of ruptured membranes is an important diagnostic aid.

In the mature fetus therefore, early diagnosis of membrane rupture allows for expediting the delivery thereby reducing infection risk to mother and baby. In the premature infant, accurate diagnosis of membrane rupture is even more important particularly if labour needs to be induced. A reliable, easy method of diagnosis of membrane rupture would be clinically useful to the obstetrician (Davidson, K. M., Clin. Obstet. Gynecol. 34:715–722 (1991); Gregg, A. R., Obstet. Gynecol. Clin. North Am. 19:241–249 (1992) and also cost saving by reducing the need for prolonged and unnecessary hospitalisation. The benefit to those patients resident in the country areas and facing transfer to a tertiary care centre for prolonged periods of hospitalisation away from home and family environment on suspicion of having premature rupture of the membranes would be considerable.

2. DETECTION OF RUPTURE OF THE AMNIOTIC MEMBRANES IN MAMMALS

Besides physical examination, current techniques for establishing the diagnosis of ruptured fetal membranes are:

(1) Determination of the vaginal pH (Gold, V., Ann. Chir. et Gynec. Fenniae. 47:22 (1927);

(2) Staining for fetal fat globules (Von. Numers, C., Acta. Obst. et Gynec. Scand. 16:249 (1936);

(3) Identification of fetal squamous cells or hairs (Phillip. E., Zmtrolbl. Gynök. 53:1618 (1929), Bourgeois, G. A., Am. J. Obstet. Gynecol. 44:80 (1942);

(4) Examination for typical crystallisation of amniotic fluid (Volet, B., et al., Gynaecologica 149:151 (1960), Borten, M., et al., Am. J. Obstet. Gynecol. 154:628 (1986);

(5) Measurement of the DAO activity of vaginal fluid (Elmfors, B., et al., J. Obst. Gynecol. Brit. Commonw. 81:361 (1974), Gahl, W. A., et al., Obstet. Gynecol. 60:297 (1982a), Bank, C. M., et al., Eur. J. Clin. Chem. Biochem. 29:742 (1992);

(6) Alpha fetoprotein (Toth, P., et al., Acta. Paaediatr. Hung. 30:399 (1990), Garite, T. J. et al., Am. J. Perinatol. 7:276 (1990);

(7) Prolactin (Kalenga, M. K., et al., Rev. fr. Gynecol. Obstet. 86:585 (1991);

(8) Human placental lactogen (Kalenga, M. K., et al., above);

(9) Amniotic fluid form of diamine oxidase (Australian Patent 622788);

(10) Fetal fibronectin (Hellemans, P., et al., Eur. J. Obstet. Gynecol. Reprod. Biol. 43:173 (1992), Lockwood, C. J. et al., New Engl. J. Med. 325:669 (1991);

(11) Intra-amniotic injection of dyes and other chemicals (Jiminez-Balderaz E. A. Bol. med. Hosp. Infant Mex. 41:P341 (1984), Davidson, K. M., Clin. Obstet. Gynecol. 34:715 (1991));

(12) Measurement of amniotic fluid volume by ultrasound (Benacerraf, B. R., J. Ultrasound. Med. 11:109 (1992), Hellemans, P., et al., Eur. J. Obstet. Gynecol. Reprod. Biol. 43:173 (1992);

(13) Oral ingestion of dye (Meyer, B. A., et al., Am. J. Perinatol. 8:297 (1991).

Methods 1–4

In accordance with Friedman, M. L., et al., (Am. J. Obstet. Gynaecol. 48:172 (1976) any three of the abovementioned methods taken together provide an accuracy of 93% although false-positive and false-negative results are frequent with all laboratory techniques which are applied in diagnosing rupture of the membranes (Larsen, L., above).

Method 5- DAO Activity

Elmfors, B., et al. (above), using the information of Tornqvist, A., et al., (Acta. Obstet. Gynec. Scand. 50:79 (1971) developed a method for the diagnosis of ruptured membranes by measuring the DAO activity in vaginal fluid. DAO activity is present in amniotic fluid but normally absent from vaginal secretions, presenting a method for diagnosing rupture of the membrane (Elmfors, B., et al. above; Gahl, W. A., et al. above). The most widely used method for collection of DAO activity in vaginal secretions is the use of blotting paper to collect the secretions and phosphate buffer to elute the enzyme (Elmfors, above). Wishart, H. M., et al. (Aust. N. Z. J. Obstet. Gynaec. 19:23 (1979) also supported the use of the procedure and found an assay to offer useful clinical information. The factors which suggest that the DAO assay may be used as an adjunct to convention tests in the diagnosis of rupture of membranes have been summarised by Gahl, W. A., et al. (above). However, the major drawback of the assay is that it depends on the measurement of enzyme activity and can give false results in the presence of interfering substances such as:

(1) urine;
(2) meconium;
(3) antiseptics;
(4) pregnancy serum;
(5) seminal fluid;
(6) haemoglobin.

These substances commonly contaminate the vagina therefore invalidating current methods which are limited by interfering substances, inadequate sensitivity and subjective interpretation of results.

Methods 6–8

Measurements of the protein alpha-fetoprotein and the hormones prolactin and human placental lactogen have been investigated by Huber, J. F., et al., (Br. J. Obstet. Gynaecol. 90:1183–1185 (1983)) but he found many positive tests in patients whose membranes were intact. This was due in part to the fact that these substances are present in maternal serum and therefore the test is positive when either serum or amniotic fluid or both are present in the vagina. Rochelson B. C. (Obstet. Gynaecol. 69:163–6 (1987)) has also found blood and serum to give false positive results with his test for the presence of alpha-fetoprotein in vaginal fluid.

Method 9- Amniotic fluid form of Diamine Oxidase

Reference may be made to Australian Patent Specification 622788 (published under WO90/10061) which refers to an assay for detection of rupture of the amniotic membrane in pregnant mammals which was based on the discovery that for the first time two forms of diamine oxidase were found—one form located in maternal serum and another form located in amniotic fluid which were glycoproteins apparently having different polysaccharide moieties and similar protein moieties. When the amniotic membrane ruptured the amniotic fluid diamine oxidase could then be detected in maternal serum for the first time however, while polyclonal antibodies were developed in relation to each glycoprotein it was apparently difficult to develop monoclonal antibodies because of similar conformational or three dimensional structures for each glycoprotein thereby providing similar epitopes.

There was also a small degree of cross reactivity with both serum diamine oxidase and amniotic fluid diamine oxidase—i.e. both would react with maternal serum to some degree. This meant that there was no guarantee that amniotic fluid diamine oxidase could not pass through the placenta or the amniotic membrane and thus be present in maternal serum even only to a slight extent.

Method 10- Fetal Fibronectin

The detection of fetal fibronectins not specific for rupture of the amniotic membranes. It has been shown to be present in vaginal fluid without rupture of the amniotic membranes (Lockwood, C. J. et al., New Engl. J. Med. 325:669 (1991)) and is best described as a test for preterm delivery. In evaluating this test (Creasy, R. K., New Engl. J. Med. 325:727 (1991)), the need for a reliable test specific for membrane rupture was clearly identified.

Methods 11–13

Dyes and other chemicals have been injected into the amniotic fluid transabdominally and their appearance looked for in the vagina (Jiminez-Balderaz, E. A. above; Davidson, P. above). These methods differ from the present invention in that they are physical methods (Hellemans, P., et al. above; Bancerraf, B. R., above) or include the injection of dyes into the pregnant mammal (Meyer, B. A., et al., above). They are not immunoassays. Due to the possibility of allergic reactions, these techniques are not without risk (Davidson, K. M. above).

3. PROTEINS PRESENT IN AMNIOTIC FLUID

A large number of proteins are present in amniotic fluid. These can derive from different tissues of origin. In particular, proteins have been described which originate from maternal serum (Sôrensen, S. Clinica. Chimica. Acta. 202:199 (1991), the placenta, amniotic fluid cells, fetal urine, fetal lung and fetal skin. The fate of most of these proteins is unknown although it is known that proteins can move from one compartment to another in pregnancy or can be present in more than one body fluid. For example, alpha-fetoprotein and albumin are found in both and fetal serum as well as amniotic fluid (Huber, J. F., et al. above), and fetal fibronectin is found in placental membrane tissue as well as amniotic fluid.

SUMMARY OF THE INVENTION

It is therefore an object of the present invention to provide an assay for diagnosis of amniotic membrane rupture or leakage of amniotic fluid which is reliable and alleviates the problems encountered in the prior art assays above.

The invention therefore provides an assay for the detection of amniotic fluid in body fluids and in particular an assay for diagnosis of rupture of the amniotic membranes or leakage of amniotic fluid in pregnant mammals and in particular pregnant women including the step of detecting the presence of PROM antigen (PROM-Ag) as hereinafter described in vaginal fluid and thereby establishing that amniotic fluid is present in the vaginal fluid. This means that the amniotic fluid can be distinguished from maternal serum.

In regard to pregnancy in females inflammation of the birth canal and in particular the cervix may cause leakage of maternal serum into the vagina. Amniotic fluid contains many proteins and it has now been surprisingly discovered by the present invention that a particular protein fraction (i.e. PROM-Ag) present in amniotic fluid may be used to differentiate amniotic fluid from other fluids present in the vagina by appropriate techniques for the detection of PROM-Ag described in detail hereinafter.

When rupture of the amniotic membranes occurs, this causes leakage of amniotic fluid into the vagina with the subsequent result that the vagina will contain amniotic fluid. It is thus evident that if the presence of an amniotic fluid protein, which is not detectable in other body fluids may be detected then a valuable tool will be provided for diagnosis of amniotic membrane rupture. This therefore provides a clear demonstration that "breaking of the water" has occurred and thus false alarms caused by vaginal leakage of other fluids may be avoided. False alarms are particularly prevalent when vaginal fluid may be leaked or emitted from the vagina after swimming or taking a bath, or if other body fluids such as maternal serum, exocoelemic fluid, tissue fluid, urine, semen or excessive vaginal fluid itself are present in larger than normal amounts.

It is believed following the present invention the PROM-Ag is detectable in amniotic fluid and is not detectable in other fluids which may be present in the vagina. This detection of PROM-Ag by appropriate techniques which include isoelectric point, sub-unit molecular weight and native molecular weight will differentiate amniotic fluid from other fluids in the vagina. However, probably the best method of measuring PROM-Ag is by the use of immunological techniques or immunoassays as described hereinafter. In this regard therefore development of an appropriate binding agent having specificity for PROM-Ag, for example an antibody which may be polycloonal or monoclonal in nature, would be of assistance in detecting PROM-Ag. Thus a specific polyclonal or monoclonal antibody for PROM-Ag will be extremely useful in detecting amniotic fluid. These antibodies will also be extremely useful in devising other methods for purifying PROM-Ag from amniotic fluid so that other monoclonal or polyclonal antibodies can be obtained by procedures well known to those skilled in the art.

It will be appreciated that antibodies that may be used in the present invention can be raised in animals to proteins obtained from animals of a different species which are different to those found in the animal in which the antibodies are raised. Such antibodies may be polyclonal or monoclonal. The techniques for producing such antibodies are readily available in but not limited to those described in publications such as Kennett, R. H., McKearn, T. J., and Bechtol, K. B. eds., Monoclonal Antibodies, Hybridomas: A new dimension in biological analyses. Plenum Press, Inc., N.Y., pp. 361–419 (1980). Further, the procedures for isolating sensitised spleen cells are well known in the art (Kennett, R. H. et al., above).

The particular myeloma cell lines employed as starting materials for producing the hybridomas of the present invention which produces monoclonal antibodies specific to the PROM-Ag are not critical to the present invention. Examples of such myeloma cell lines include SP2/0 Ag 14 (Fiscus, S. A., et al., J. Clin. Micro. 22: 395–401 (1985)), and FOX-NY (Taggert, R. T., et al., Science 219:1228–1230 (1983)), P3×G3 Ag 8 (Kohler, G., et al., J. Immunol. 6: 292 (1976)), 45.6T61.7. (Margulies, D., et al., Cold Spring Harbor Symp. Quant. Biol. 41:781 (1977)), WI-L2-729HFZ (Strike, L. E., et al., J. Immunol. 132:1798 (1984)), MPC-11 (ATCC No. CCL 167), J558 (ATTCC. No. TIB6), P3.6.2.8.1 (ATCC No. TIB 8), P1.17 (ATCC No. TIB 10), C1.18.4 (ATCC No. TIB 11), RPC5.4 (ATCC No. TIB 12), HOPC1F/12 (ATCC No. TIB 13), RPMI18226 (ATCC No. CCL 155) and ISM2.7 (Schuster, J. F., et al., Human Immunol. 9:137–143 (1984)).

The production of hybridoma cell lines employing the sensitised spleen cells and well-known myelomas can be performed using well-known procedures (Kennett, R. H., et al., above, Taggart, R. T., above, Cole, S. P. C., et al., Mol. Cell. Bioch. 62:109–120 (1984)).

The production of monoclonal antibody specific to PROM-Ag is not limited to that obtained from murine hybridomas and can include monoclonal antibodies obtained from human, rat or other animal hybridomas.

Antibody fragments, such as (Fab)$_2$, Fab and FV fragments, can be used in place of intact antibody molecules. Genetic engineering techniques can also be used to produce appropriate antibodies and fragments.

Techniques for producing immunoassays are readily available in, but not limited to, those described in Ishikawa, E., Biochem. 20:375 (1987).

PROM-Ag antigen and antibody specific thereto can be labelled with an enzyme in an ELISA or EIA such as horseradish peroxidase (hereinafter "HRPO"), alkaline phosphatase, urease and luciferase by procedures well known in the art. Alternatively, the PROM-Ag and antibody specific thereto can be labelled with a fluorescent marker in an FIA such as fluorescein, rhodamine, Texas Red (Molecular Probes, Inc.) or ANS (1-anilino-8-naphthalene sulfonate). Use may also be made of an RIA including radiolabels such as $^{125}$I, $^{14}$C, $^{32}$P or $^{3}$H by procedures well known in the art.

Other labelling systems which may be used include insoluble particulate labels, especially particulate direct labels such as minute coloured latex particles, metallic sols (e.g. gold sol) and dye sols.

Enzymes may be conjugated to antibodies or other proteins using any of a variety of coupling reactions. The reaction conditions vary depending upon the exact coupling reagent being used. The coupling reagents include, for example, di-isocyanates, di-aldehydes, carbodiimides, isothiocyanates, mercurics, imidoesters and bismaleimides. These coupling reactions are well known in the art. (Kennedy, J. H., et al., Clin. Chim. Acta 70:1 (1976)).

Many uses of enzyme-conjugated antibodies have been reported. Assays using enzyme-conjugated antibodies range from hormones such as human chorionic gonadotrophin (Van Weemen, B. K. et al., Int. Arch. Allegy Appl. Immunol. 54:88 (1987)) to infectious diseases (Holmgren, J., et al., Infect. Immunity 7:759 (1977), and Voller, A., et al. The Enzyme-Linked Imminoabsorbent Assay (ELISA), Dynatech Laboratories, Inc. (1979)).

Fluorescent compounds may also be covalently linked to proteins using reagents similar to those employed with enzymes. An example of such a reagent is fluorescein isothiocyanate, wherein the fluorescein group is linked to the isothiocyanate coupling reagent. There are a large number of fluorescent markers available and well known to ones skilled in the art (Stryer, L., Ann. Rev. Bioch. 47:819 (1978), Kennedy, J. H. et al., Clin. Chim. Acta 70:1 (1976), and Wicker, R., Ann. N.Y. Acad. Sci. 177:490 (1971)).

Biotinylation of proteins is easily accomplished using the procedure of Goding, J. W., J. Immunol. Methods 39:285 (1980). Typically, 50–250 µg of biotin succinimide ester is required per milligram of protein. Avidin is coupled to other proteins, such as HRPO. Avidin binds strongly to biotin. Uses for the avidin-biotin system are similar to those listed for enzyme-conjugated antibodies.

Radiolabelled proteins can be obtained using a variety of reagents and labels. Examples of the well-known $^{125}$I labelling kits include Enzymobead radioiodination reagent (Bio-Rad Laboratories) and Iodo-Gen reagent (Peirce Chemicals) (Berson, S. A., et al., J. Clin. Invest. 35:170 (1956) and Skelley, D. S., Clin. Chem. 19:146 (1973)).

Use may also be made of immunoassays based on agglutination including latex beads or chemiluminscence.

The specific measuring means will depend on the label employed. Such measuring means are well known in the art as exemplified by the above cited references.

The way to obtain an estimate of the amount of antigen present is to measure the test sample relative to a known quantity of standard antigen.

It is also appropriate to bind antigen or antibody to a suitable solid support. In this case it is preferred that the antibody is bound to the solid support. Examples of solid supports useful in the present invention include polystyrene or polypropylene microtiter wells; polyethylene, polyvinyl, polypropylene, polycarbonate, polystyrene, or glass test tubes, capillary tubes, dipsticks, or beads, latex beads; nitrocellulose; nylon; cellulose; polyacrylamide; cross-linked dextrans and monocrystalline glass.

Very suitable assay formats using the principles of immunochromatography and particulate direct labels are disclosed in EP-A-291194 and EP-A-383619, the content of which is included herein by reference.

Optimal conditions for coating a solid support are best determined by checkerboard titrations using reference reagents. At a minimum, one must test the concentration of antigen or antibody, the time of coating, temperature, buffer conditions and pH. Many antigens can be bound by passive absorption (Voller, A., et al., above). Practical aspects are well known to those skilled in the art and guides have been published relative thereto. (Voller, A., et al., above).

The present invention therefore can be utilised in the following cases:

(i) where there is premature rupture of the amniotic membrane without blood loss;

(ii) where there is premature rupture of the amniotic membrane with blood loss;

(iii) where there is lesion of the birth canal and particularly the cervix without rupture of the amniotic membrane;

(iv) where there is no rupture of the amniotic membrane and no lesion; and (v) where there is rupture as well as a lesion.

In the case of (i), (ii) and (v) above a test for presence of PROM-Ag in the vaginal fluid would be positive.

In the case of (iii) and (iv) above a test for PROM-Ag would be negative.

It is therefore within the scope of the present invention that diagnosis of one or all of the above cases (i) to (v) are contemplated.

The assay of the invention in a preferred form may include the following steps:

(a) obtaining a sample of vaginal fluid from a pregnant female;

(b) reacting the sample with antibody derived from PROM-Ag; and (c) detection of reactivity by a signal amplification.

The invention may also include within its scope a test system or kit for the use with the method described above. This may include a PROM-Ag antibody which is immobilised to an inert surface such as a test tube or other suitable vessel. The antibody which is suitably a monoclonal or polyclonal antibody may be physically or chemical bound to the inert surface.

A further component of the reaction system may be a conjugated polyclonal or monoclonal antibody for PROM-Ag which has a suitable label attached thereto. Upon reaction of the PROM-Ag with a polyclonal or monoclonal antibody then conjugated polyclonal or monoclonal antibody may also be bound to the PROM-Ag and the label subsequently detected by any suitable means as described above. Thus if the label is an enzyme a suitable enzyme substrate may be used. Alternatively RIA, FIA, agglutination, chemiluminescence, membrane or a dipstick detection may be used depending upon the label.

The use of some of these techniques for PROM-Ag detection may be limited by prior publications covering the techniques themselves (Yoshitake, S., Imagawa, M., et al., J. Biochem. 92:1413 (1982), Goding, J. W. ed. Monoclonal Antibodies: Principles and Practices. Academic Press Inc. London (1986)). However, this disclosure also limits the use of these techniques for the detection of PROM-Ag, as this particular application of these techniques could not be foreseen at the time of their publication.

In regard to the foregoing it will also be appreciated that the term "rupture" may also include within it scope a perforation of the amniotic membrane which does not lead to complete rupture or breakdown thereof. In some cases a perforation could well exist in the amniotic membrane resulting in leakage of amniotic fluid but without resulting in complete rupture or breakdown of the membrane.

In another aspect of the invention, there is also provided a protein that can be obtained from amniotic fluid that has now been characterised by a variety of physico-chemical methods and that these physico-chemical methods may be used to clearly differentiate this protein from others present in vaginal fluid.

This protein (PROM-Ag) located in amniotic fluid has also been characterised by possessing the following physical properties:

(i) a sub-unit molecular weight of approximately 55,000 daltons performed by SDS-PAGE with gels of different acrylamide concentrations;

(ii) a native molecular weight analysis as determined by gel permeation chromatography and which revealed an apparent molecular weight of approximately 330,000 daltons;

(iii) isoelectric focusing studies revealed a protein with a band observed having an isoelectric point of 4.9; and (iv) a monoclonal antibody raised to PROM-Ag had no reactivity to maternal serum proteins when tested by a sandwich ELISA assay but had activity to amniotic fluid.

It will also be appreciated that the invention includes within its scope a method of purification of PROM-Ag from a suitable source of amniotic fluid. In particular, proteins are purified by a single or sequential use of techniques which separate groups of proteins from one another depending on their possession of a particular physical or chemical property, biological or chemical activity or immunoreactivity.

Such techniques include:

(1) Gel filtration (Schmidt, A. M., J. Biol. Chem. 267:14987 (1989), Metsarne, K., et al., Clinica. Chimica. Acta. 180:221 (1989);

(2) Electrophoresis (Carpenter, H. C., et al., Electrophoresis. 7:221 (1986);

(3) Affinity chromatography (Cuatrecasas, P., J. Biol. Chem. 245:3059 (1970);

(4) Ion exchange chromatography (Iizuka, K., et al., Ann. Clin. Biochem. 28:373 (1991), Clark, P. I., et al., Clin. Chim. Acta. 69:361 (1976);

(5) Hydroxylapatite chromatography (Stanker, L. H., et al., J. Immunol. Methods. 76:157 (1985), Chertov, O., et al., Biomed. Sci. 1:499 (1990);

(6) Thiophilic adsorption (Sulk, B., et al., J. Immunol. Methods. 149:165 (1992).

Other techniques which may be utilized include gel permeation chromatography, immunoabsorption or electroelution.

It is apparent that using such techniques a protein can be obtained in a highly purified form from a complex mixture of proteins. However, such techniques applied randomly to a complex mixture of proteins such as those found in amniotic fluid will lead to the purification of a different protein or groups of protein depending on the procedure used and the fractions selected following each stage in the process.

A particular method for purification of PROM-Ag from amniotic fluid includes the following steps:

(i) reaction of amniotic fluid with ammonium sulphate;

(ii) centrifuging the product of reaction (i) and obtaining the resulting pellet or precipitate;

(iii) resuspending the pellet or precipitate in buffer and passing the resulting solution through a column of DEAE Affi-Gel Blue;

(iv) testing unbound fractions after passage through the column for the presence of a protein of sub-unit molecular weight of approximately 55,000 daltons by SDS-page electrophoresis; and (v) concentrating fractions having said molecular weight of 55,000 daltons and passing said concentrated fractions through a Sephacryl S-200 column and collecting fractions with a molecular weight of 330,000.

Lanes 1, 2 and 8: Molecular weight standards [(BIORAD) Arrowheads]; 106,000, 80,000, 49,500, 32,500, 27,500, 18,500 Da (top to bottom).

3 Amniotic fluid.

4 Ammonium sulphate pellet of amniotic fluid.

5 Concentrated eluate from DEAE Affi-Gel Blue column.

6,7 Ammonium sulphate pellets from two material sera.

9 Molecular weight standards (Pharmacia: 94,000 (missing), 67,000, 43,000, 30,000, 20,000, 14,400 Da (top to bottom).

Figure 2:
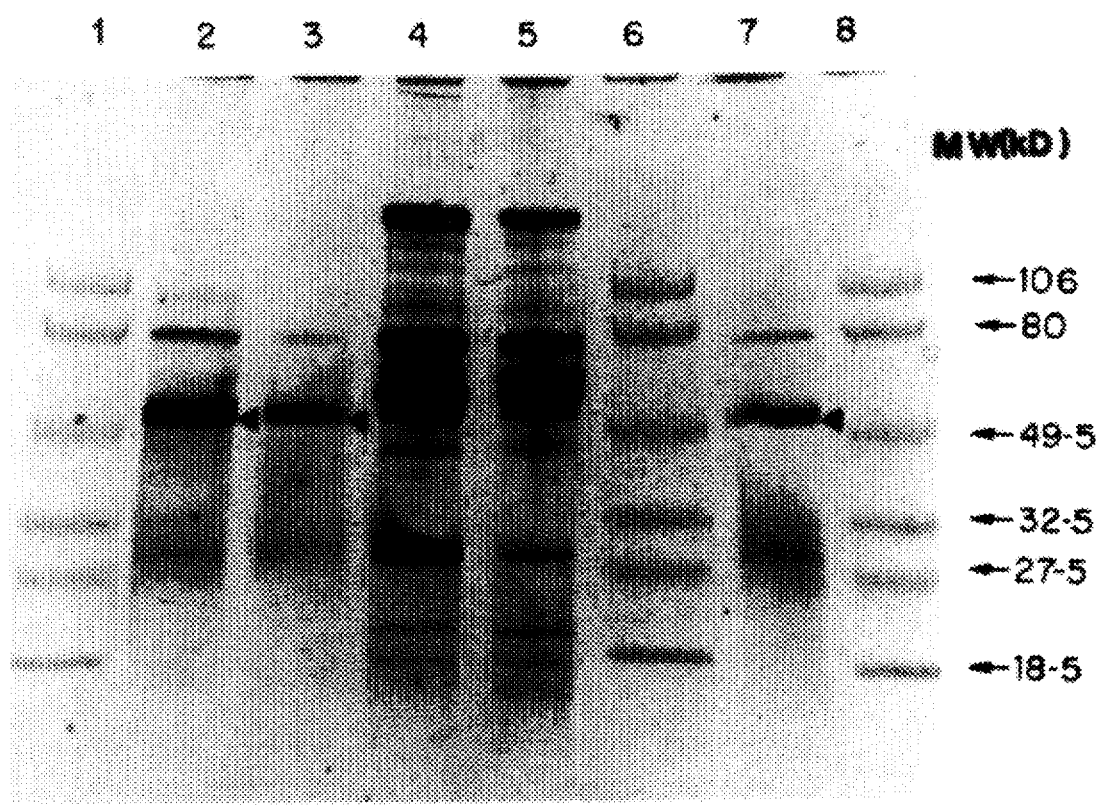

FIG. 2 demonstrates that the protein is substantially pure with only minor contaminates at subunit molecular weights of 82,000 and 30,000 DA and one major contaminant of 57,000 Da. Amniotic fluid proteins are denatured with SDS/mercaptoethanol during the purification of PROM antigen (see arrows) on 40–15 % SDS-PAGE gradient gels.

Lanes 1, 6 and 8: Molecular weight standards [(BIORAD Arrowheads)]: 106,000, 80,000, 49,500, 32,500, 27,500, 18,500 Da (top to bottom).

2 Eluate from Sephacryl S-200 column used for immunization.

7 Eluate from Sephacryl S-200 column.

4, 5 Material serum supernatant following ammonium sulphate precipitation.

Figure 3:
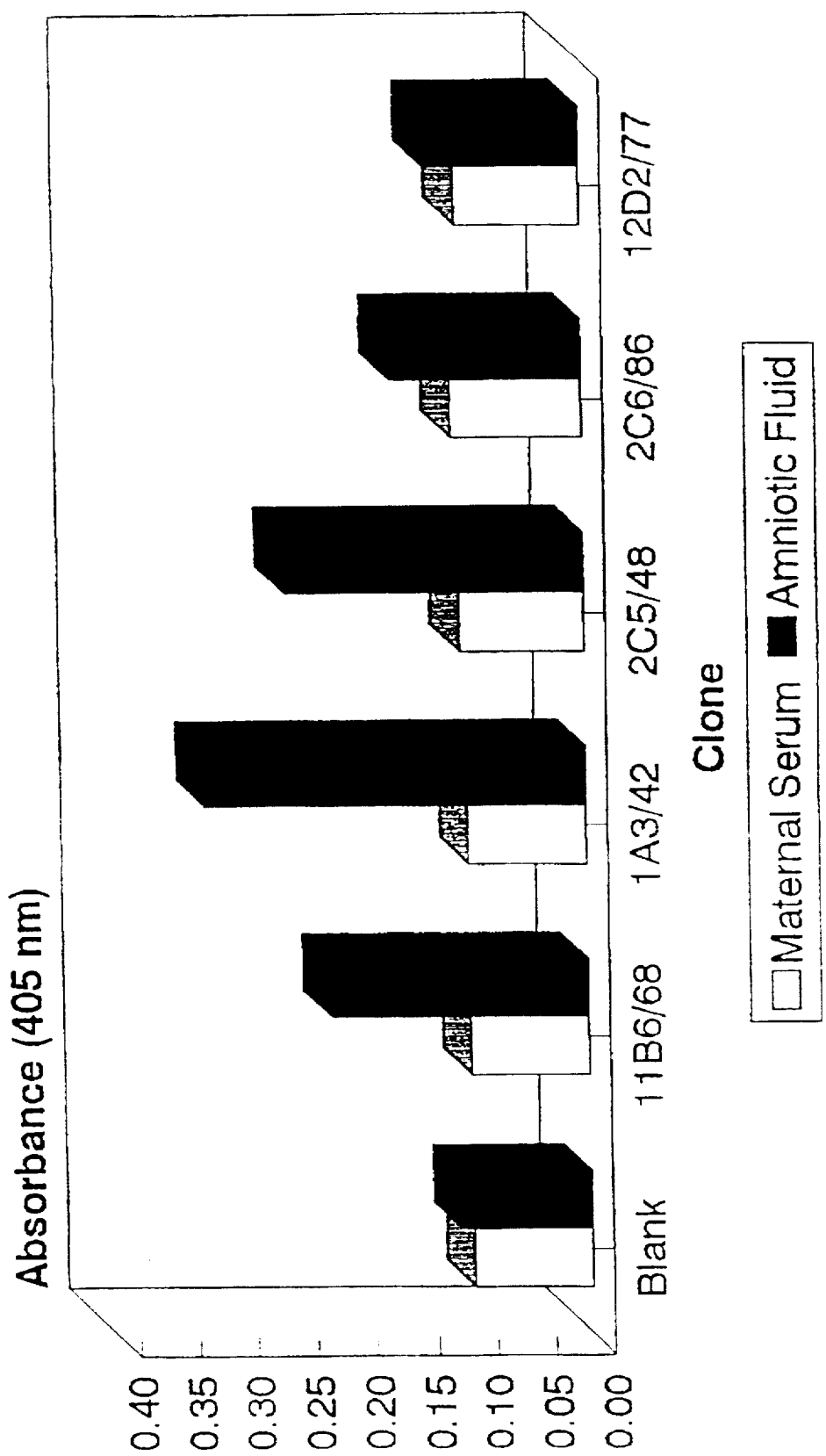

FIG. 3 illustrates the reactivity of hybridoma supernatants with maternal serum and amniotic fluid by indirect on-site ELISA.

Figure 4:
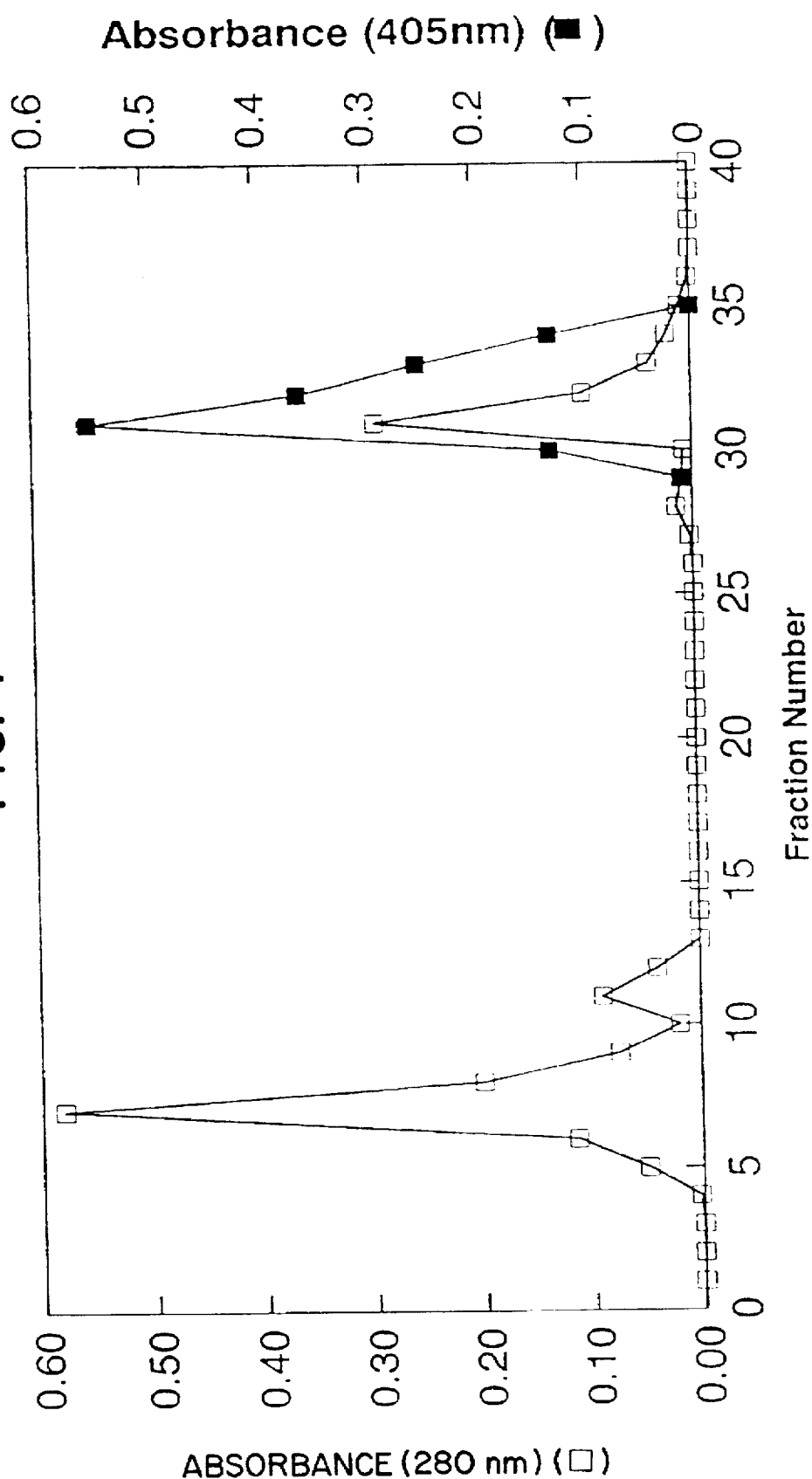

FIG. 4 shows the fractions resulting from the isolation of monoclonal immunoglobulin from ascitic fluid on a hydroxylapatite column with a 50–500 mM linear gradient of sodium phosphate buffer (pH 7.0).

Figure 5:
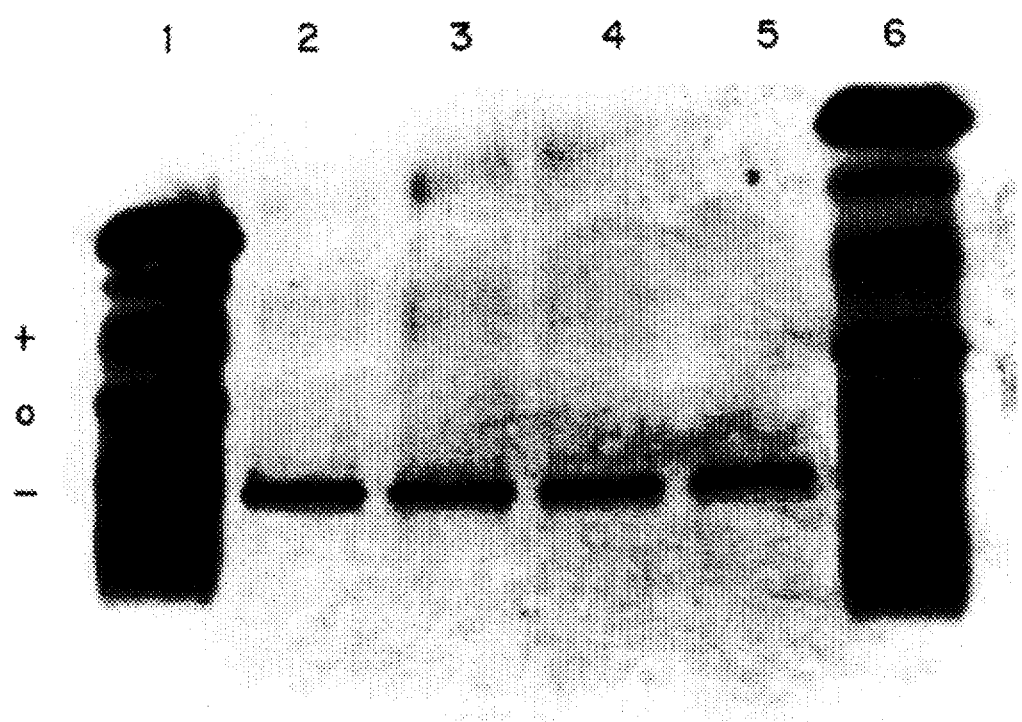

FIG. 5 shows an agarose gel electrophoresis of monoclonal antibody following hydroxylapatite chromatography.

Lanes 2 and 7: Two random term amniotic fluids.

3–6 Purified IgG fractions from hydroxylapatite column. Fractions correspond to fractions 30–33 as shown in FIG. 4.

Figure 6A:
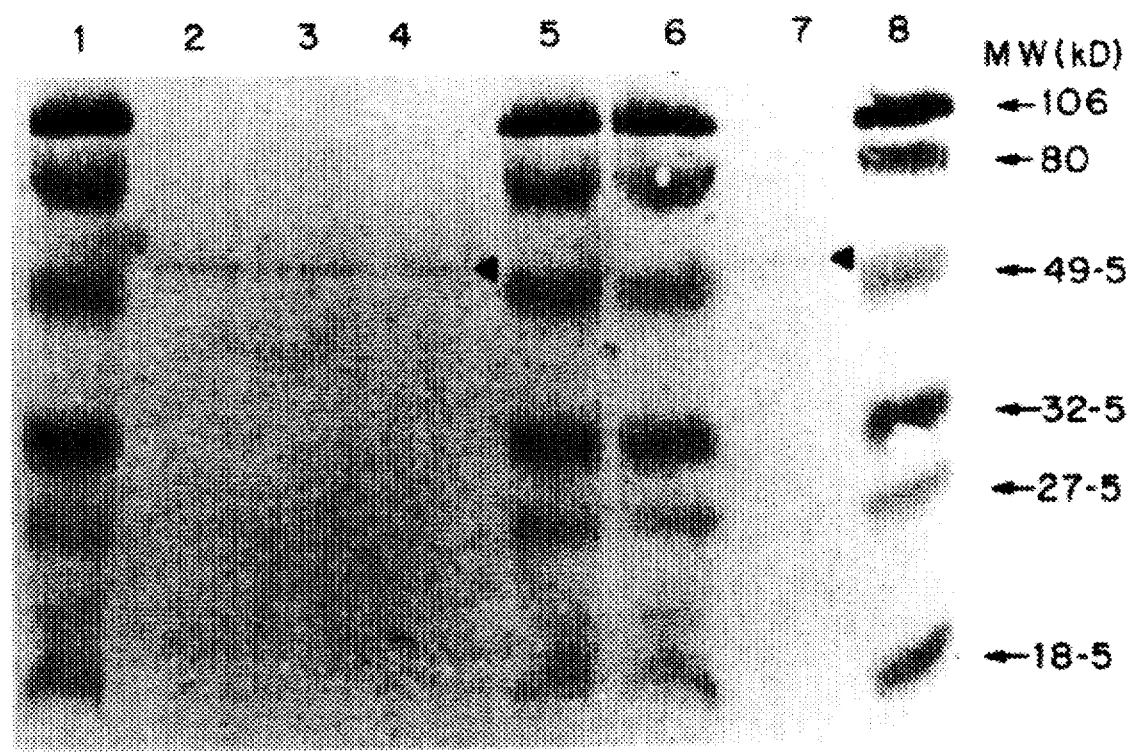

FIG. 6A shows the estimation of subunit molecular weight of PROM antigen by Western blot analysis with monoclonal 1A3-HRPO conjugate. Following incubation with SDS/mercaptoethanol, electrophoresis was performed on a 4–15% SDS-PAGE gradient gel.

Lanes 1, 5, 6 and 8: Prestained low range molecular weight standards (BIORAD): 106,000, 80,000, 49,500, 32,500, 27,500, 18,500 Da (top to bottom).

2, 3, 4 and 7: Four random amniotic fluids purified by Sephacryl S-200 column chromatography.

Figure 6B:
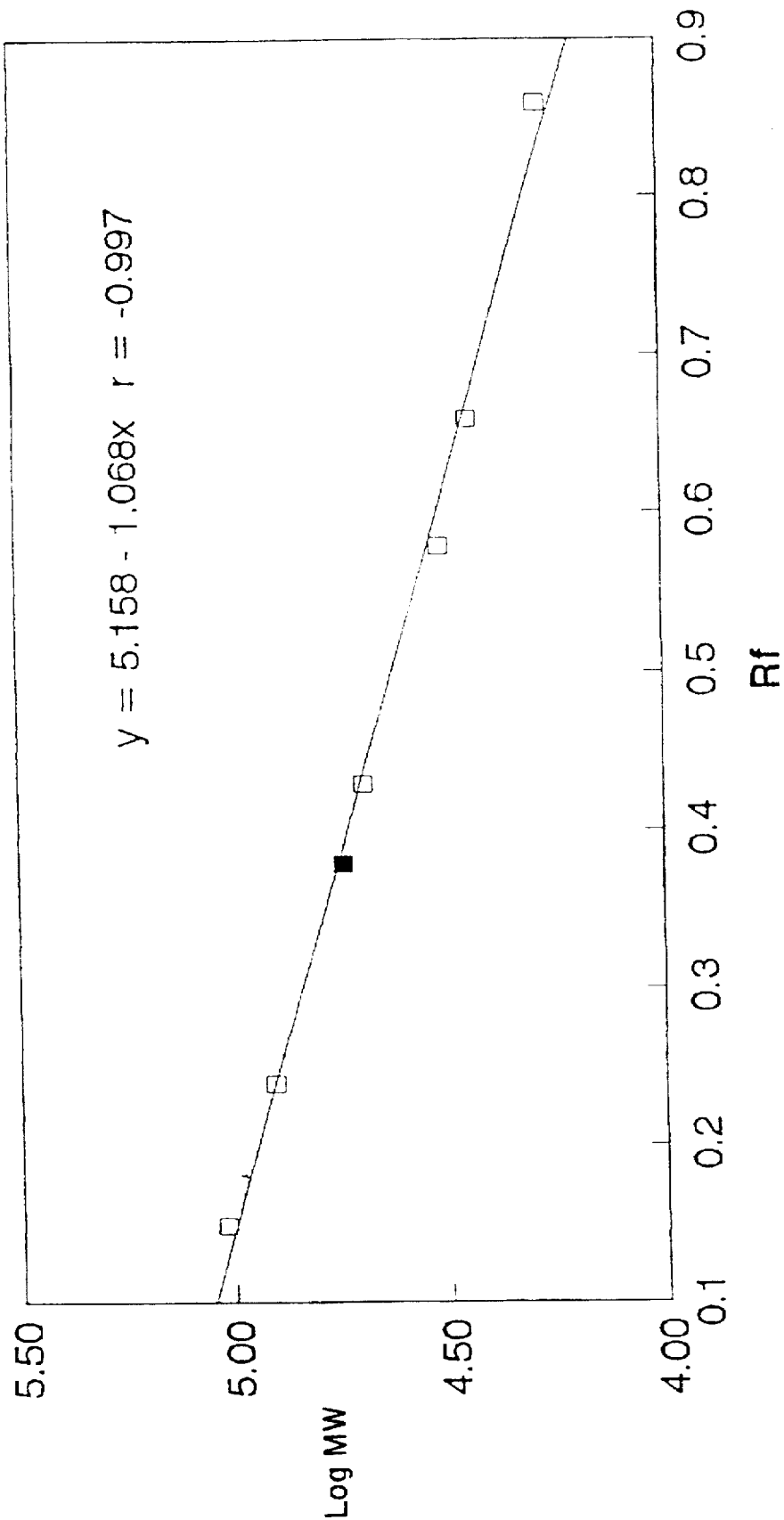

FIG. 6B shows a standard curve constructed from FIG. 6A.

Figure 7A:
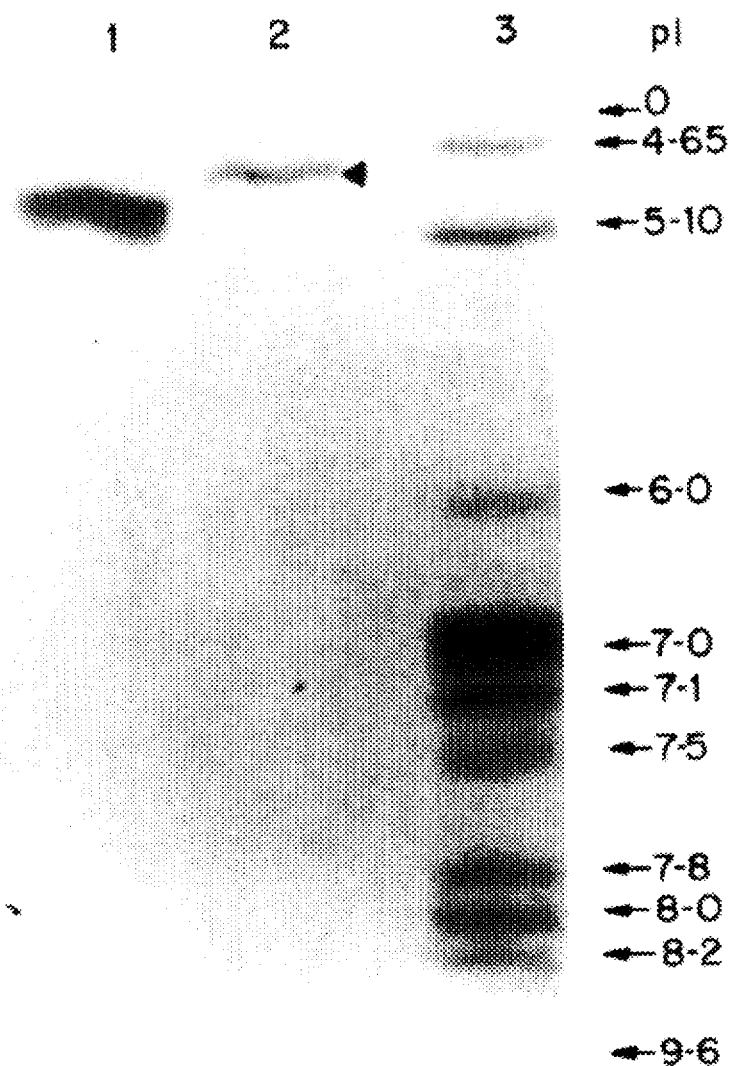

FIG. 7A shows only one major band of reactivity against purified protein. Estimation of isoelectric point of PROM antigen is obtained by western blot analysis with 1A3-HRPO conjugate. Isoelectric focusing was performed on an agarose gel pH range of 3–10.

Lane 1: IEF standards (BIORAD) stained for protein; pI's are 4.65, 5.10, 6.0, 7.0, 7.1, 7.5, 7.8, 8.0, 8.2 and 9.6 (top to bottom).

2 Purified PROM antigen stained with 1A3-HRPO conjugate.

3 A random term amniotic fluid blotted and stained for protein.

Figure 7B:
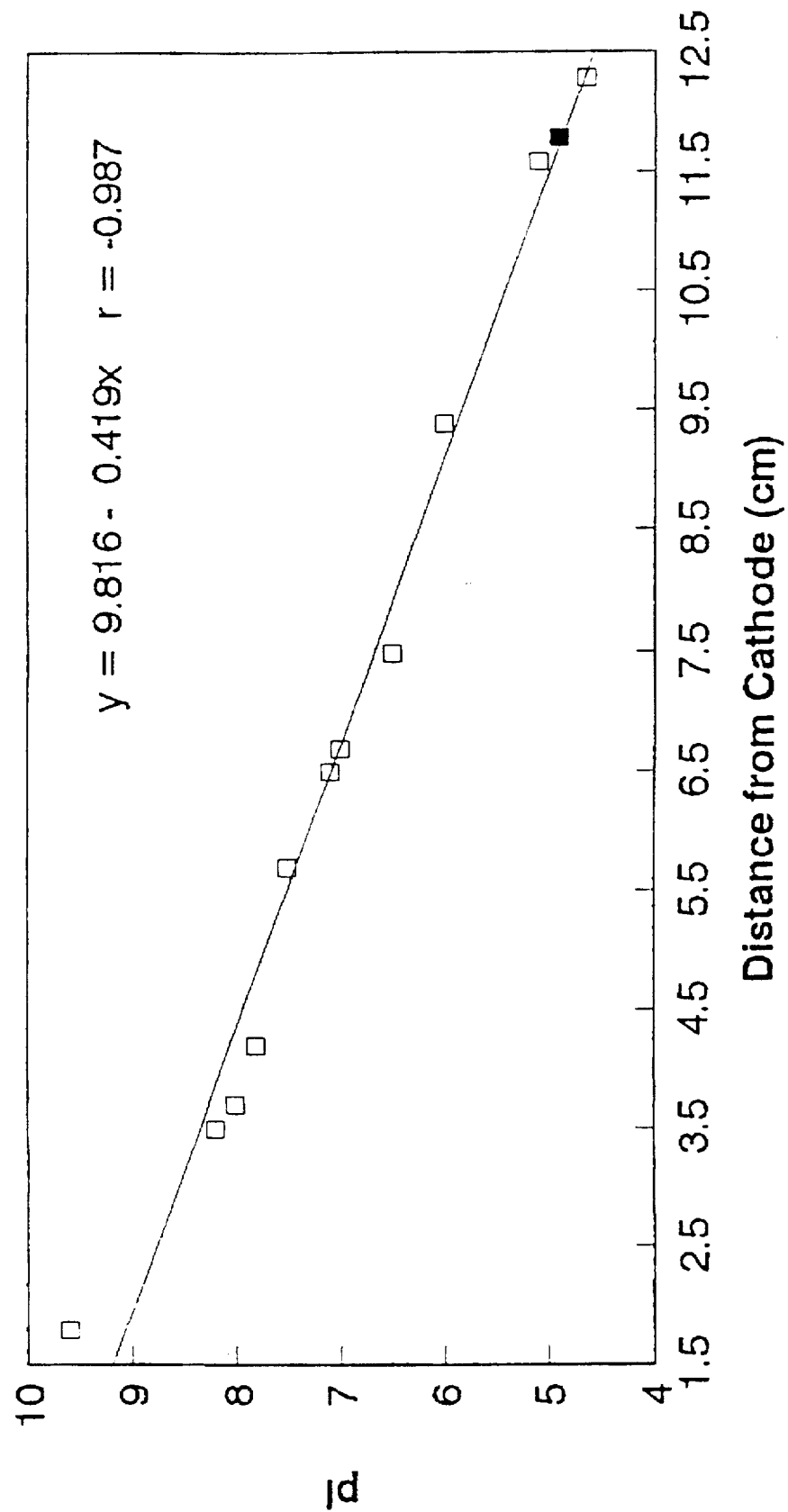

FIG. 7B shows a standard curve constructed from FIG. 7A.

Figure 8A:
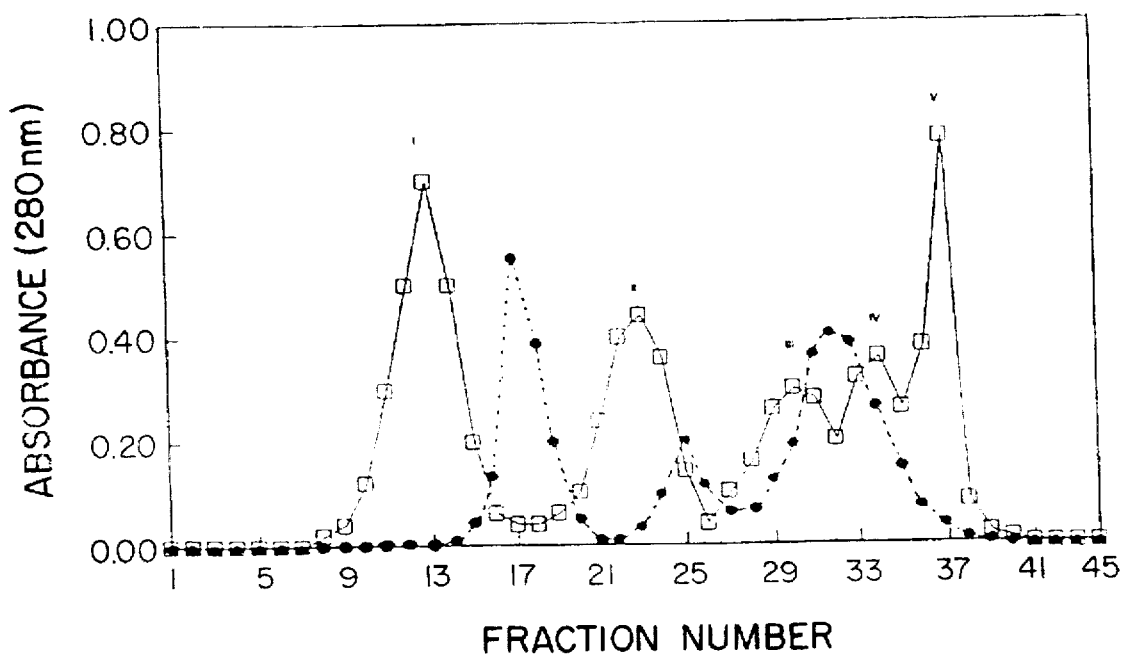

FIG. 8A shows the elution profile of post DEAE Affigel Blue fractions of amniotic fluid from Sephacryl S-200 column.

Figure 8B:
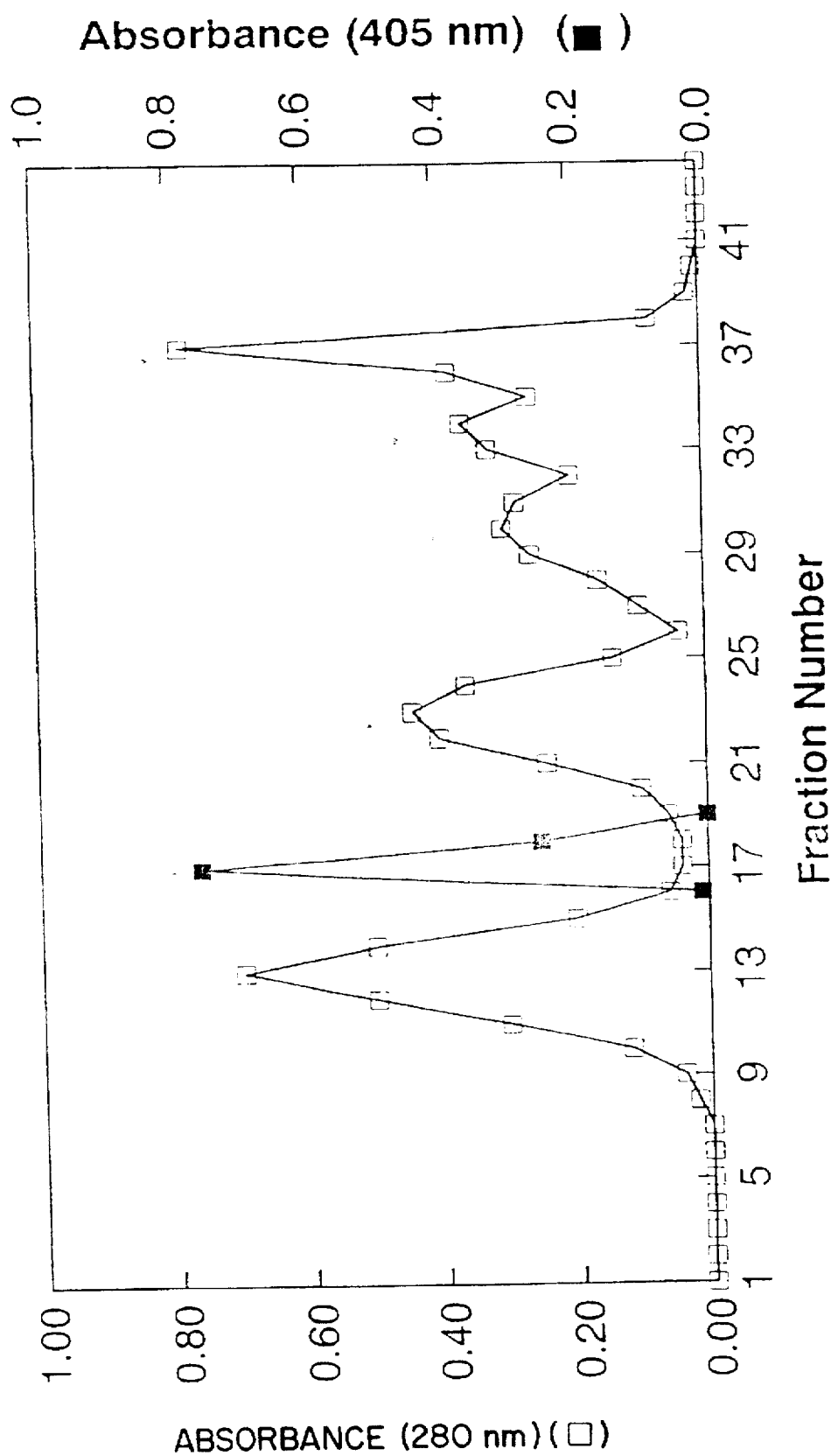

FIG. 8B illustrates the estimation of the native molecular weight of PROM antigen by gel permeation chromatography on a Sephacryl S-200 column.

Figure 8C:
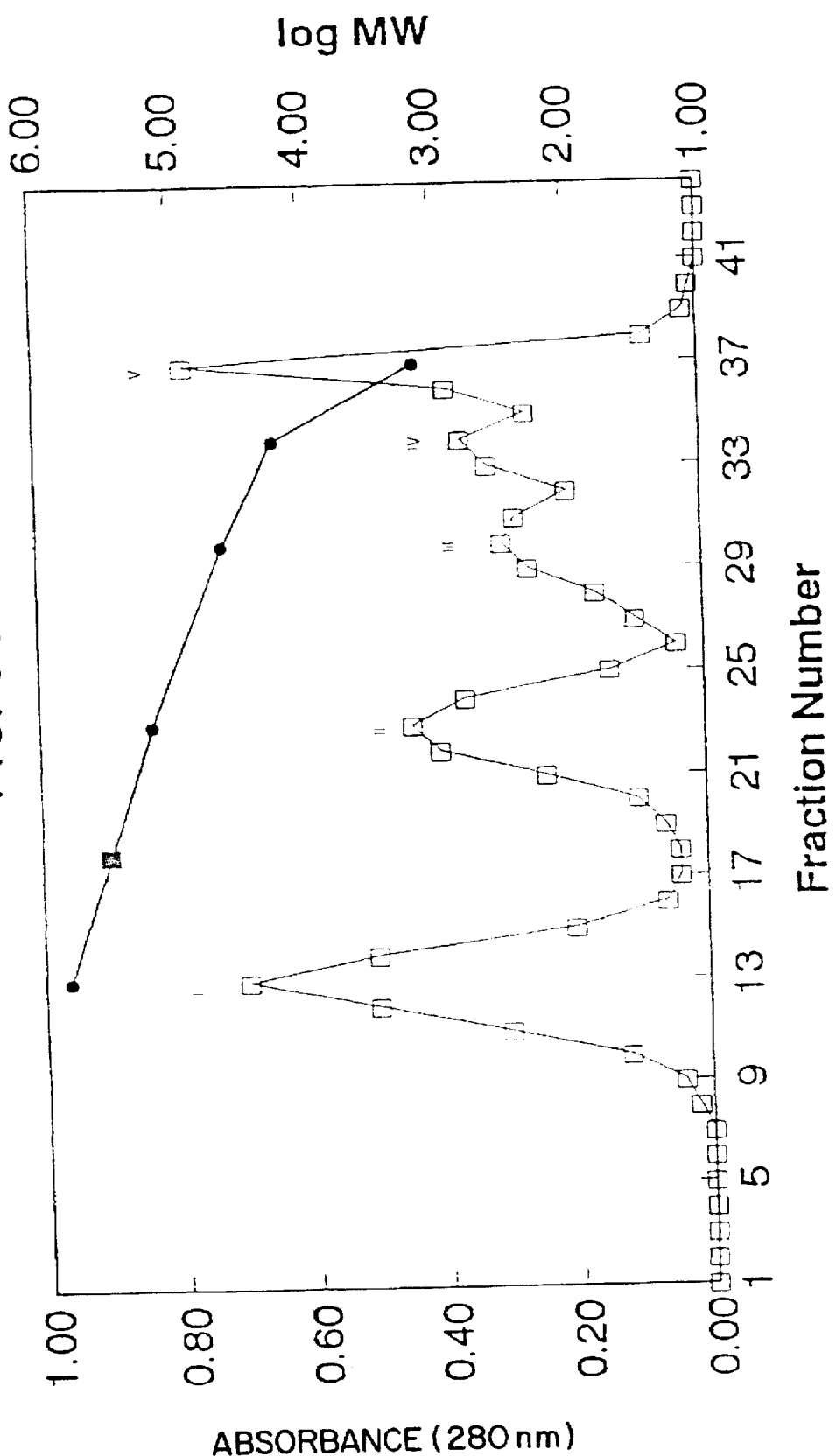

FIG. 8C illustrates the estimation of the native molecular weight of PROM antigen from molecular weight standards passed through a column of Sephacryl S-200.

Figure 9:
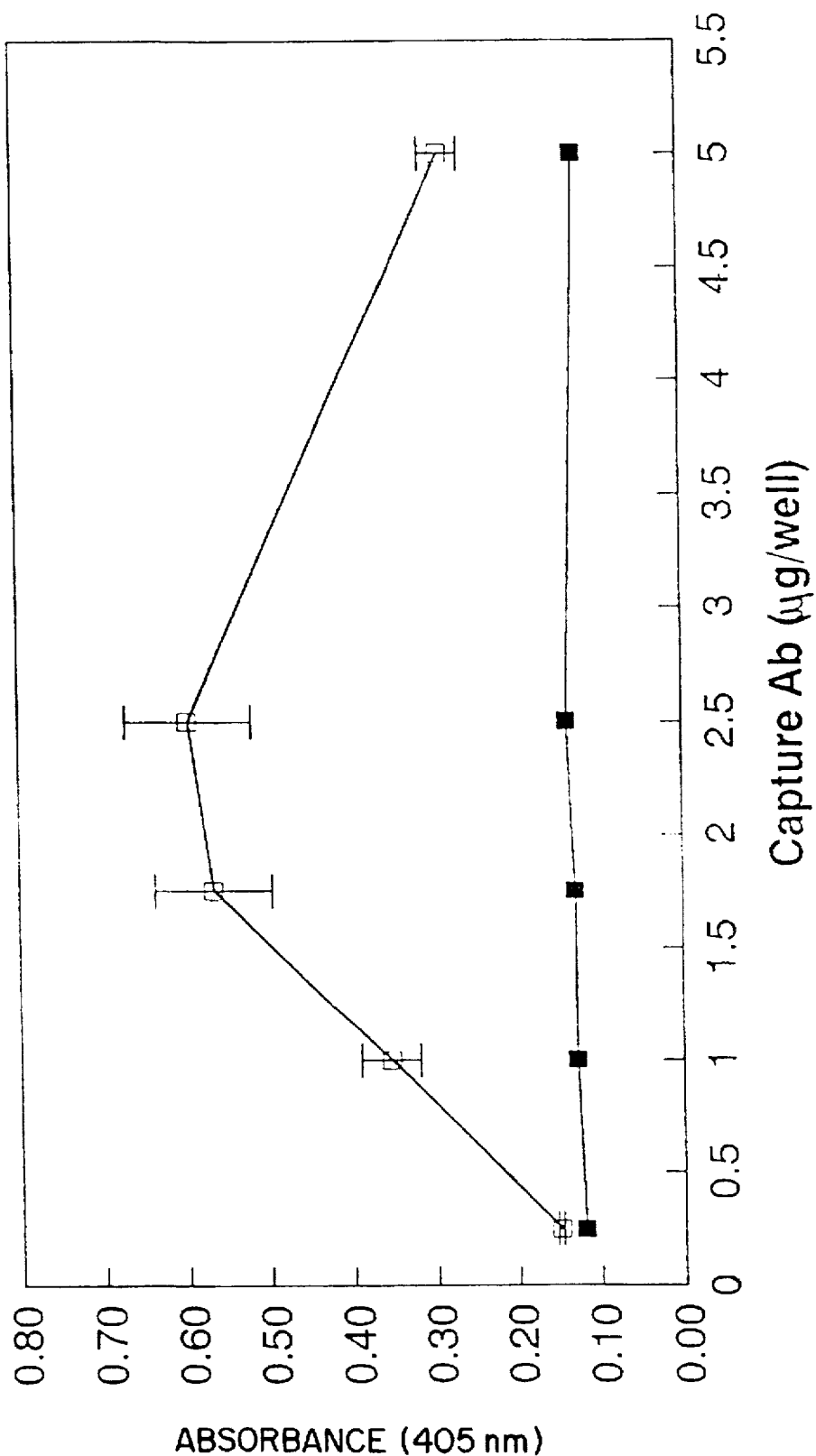

FIG. 9 shows the effect of varying capture antibody concentration used on coating wells in the detection of three amniotic fluids and three maternal sera.

Figure 10:
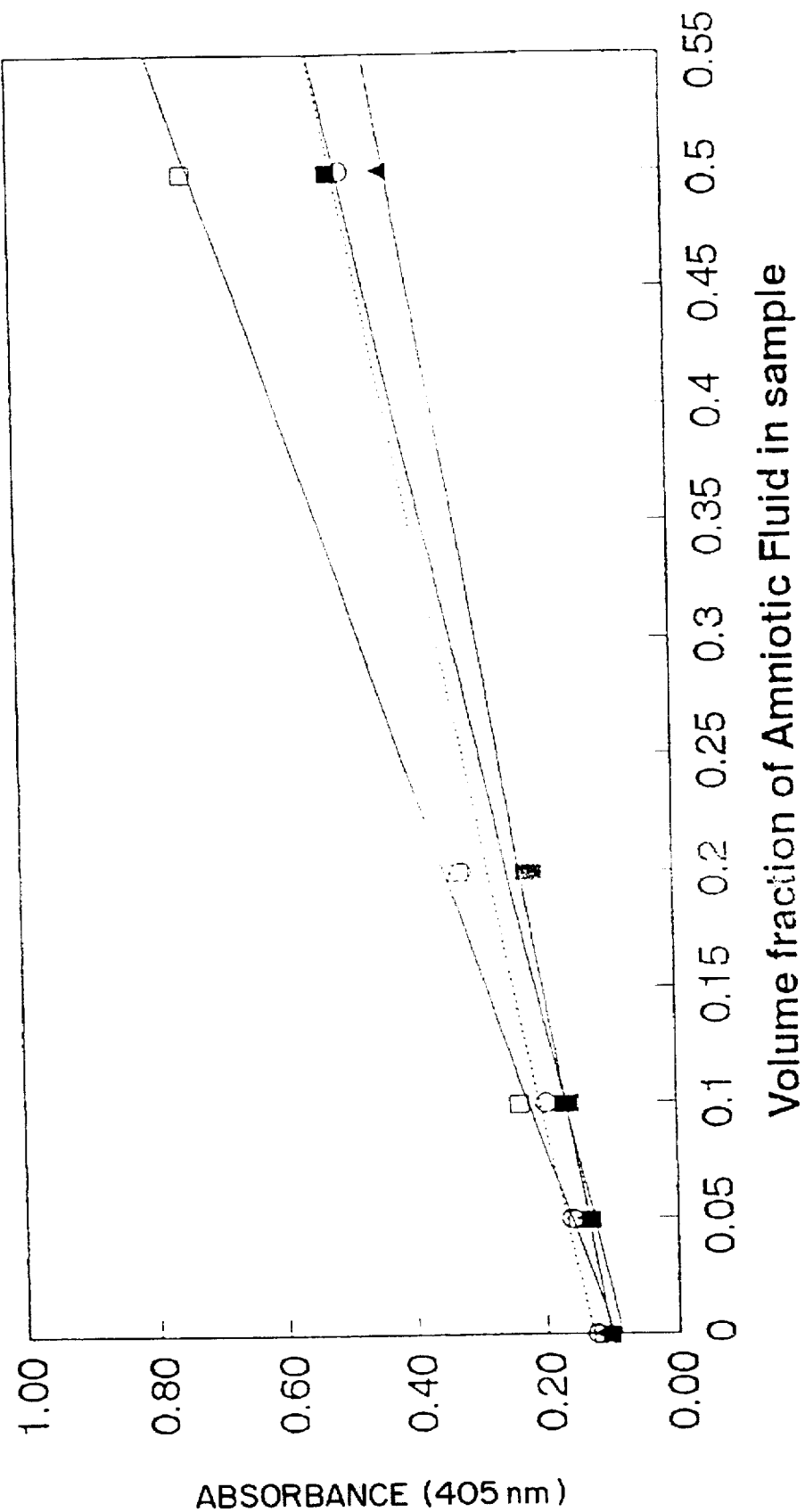

FIG. 10 shows the effect of four different blocking agents on the reactivity of serial dilutions of PROM antigen in an amniotic fluid pool.

Figure 11:
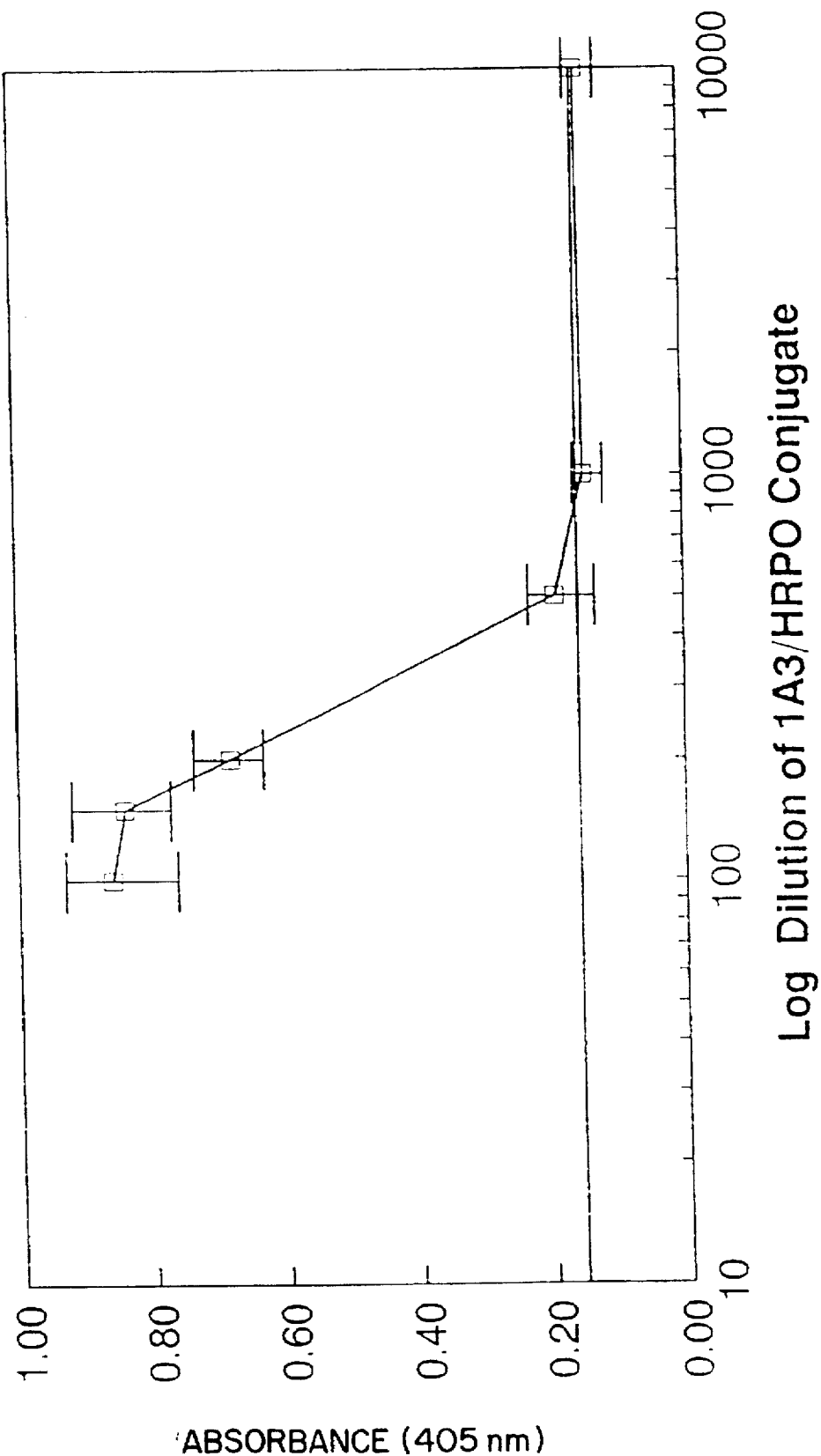

FIG. 11 shows the effect of dilution of the 1A3-HRPO conjugate on the reactivity of five random amniotic fluids.

Figure 12:
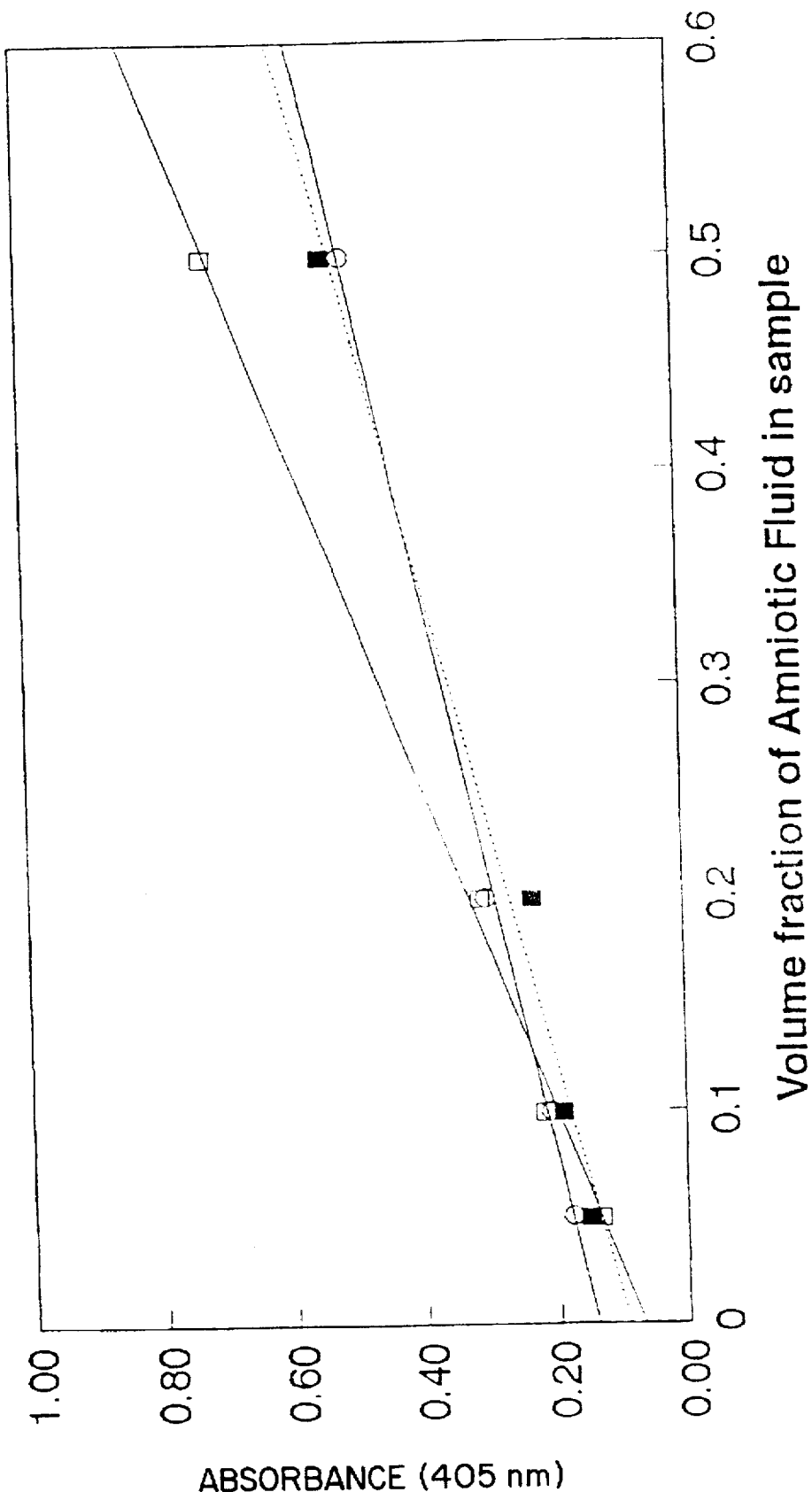

FIG. 12 shows the effect of three different sample diluents upon the reactivity of an amniotic fluid pool.

Figure 13:
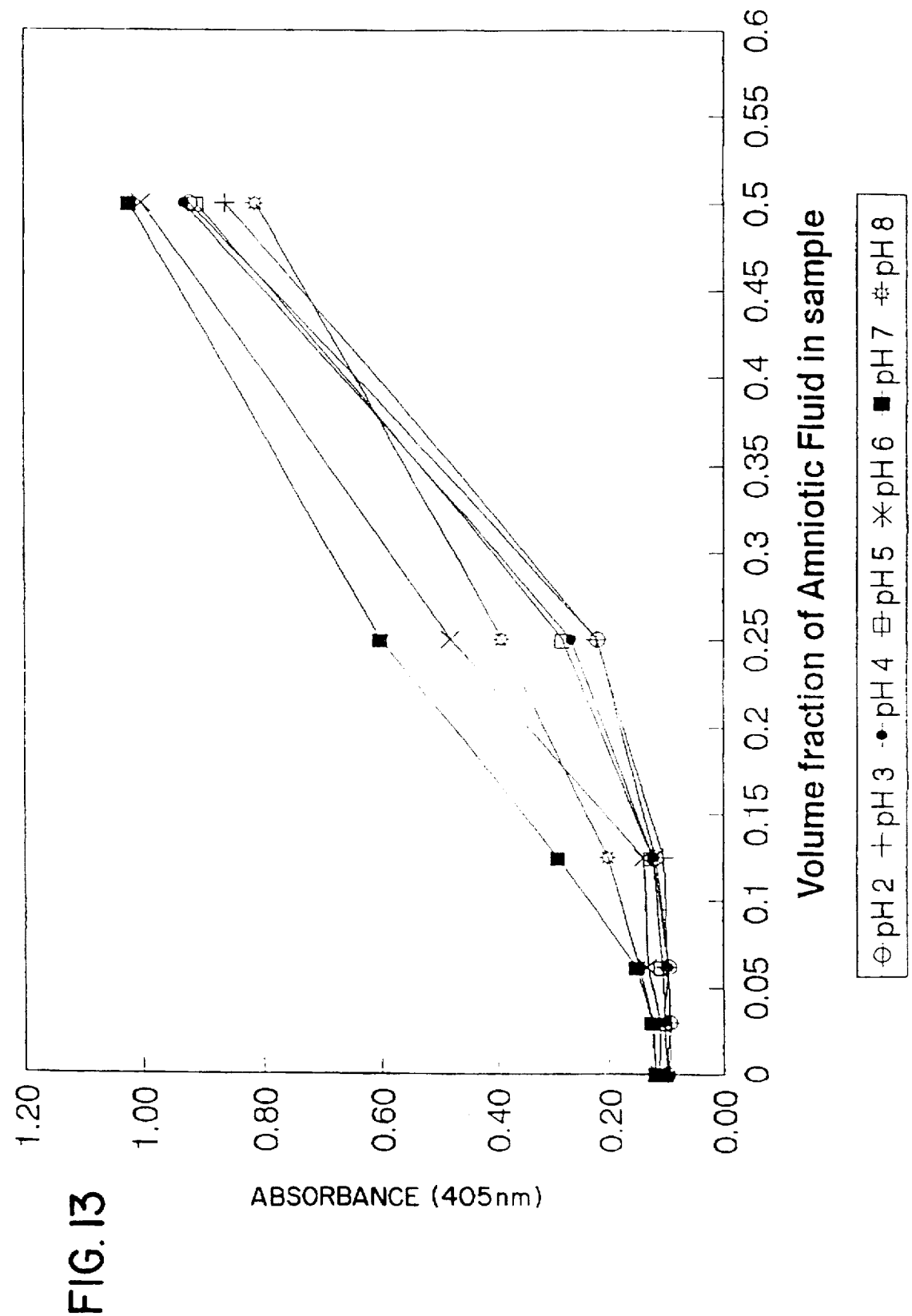

FIG. 13 shows the effect of sample diluent pH on the reactivity of serial dilutions of an amniotic pool.

Figure 14:
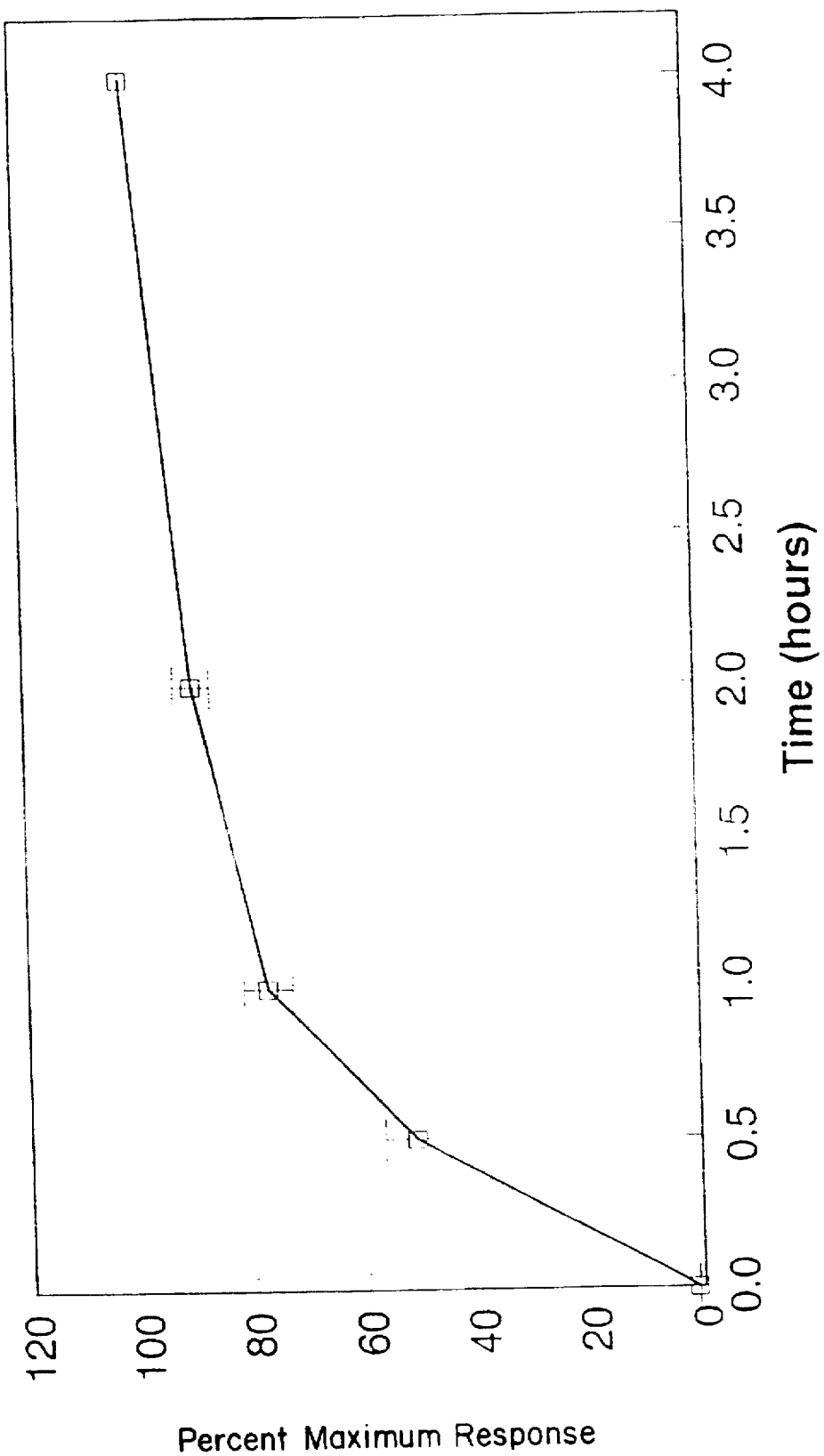

FIG. 14 shows the effect of varying sample incubation time on the reactivity of three amniotic fluids.

Figure 15:
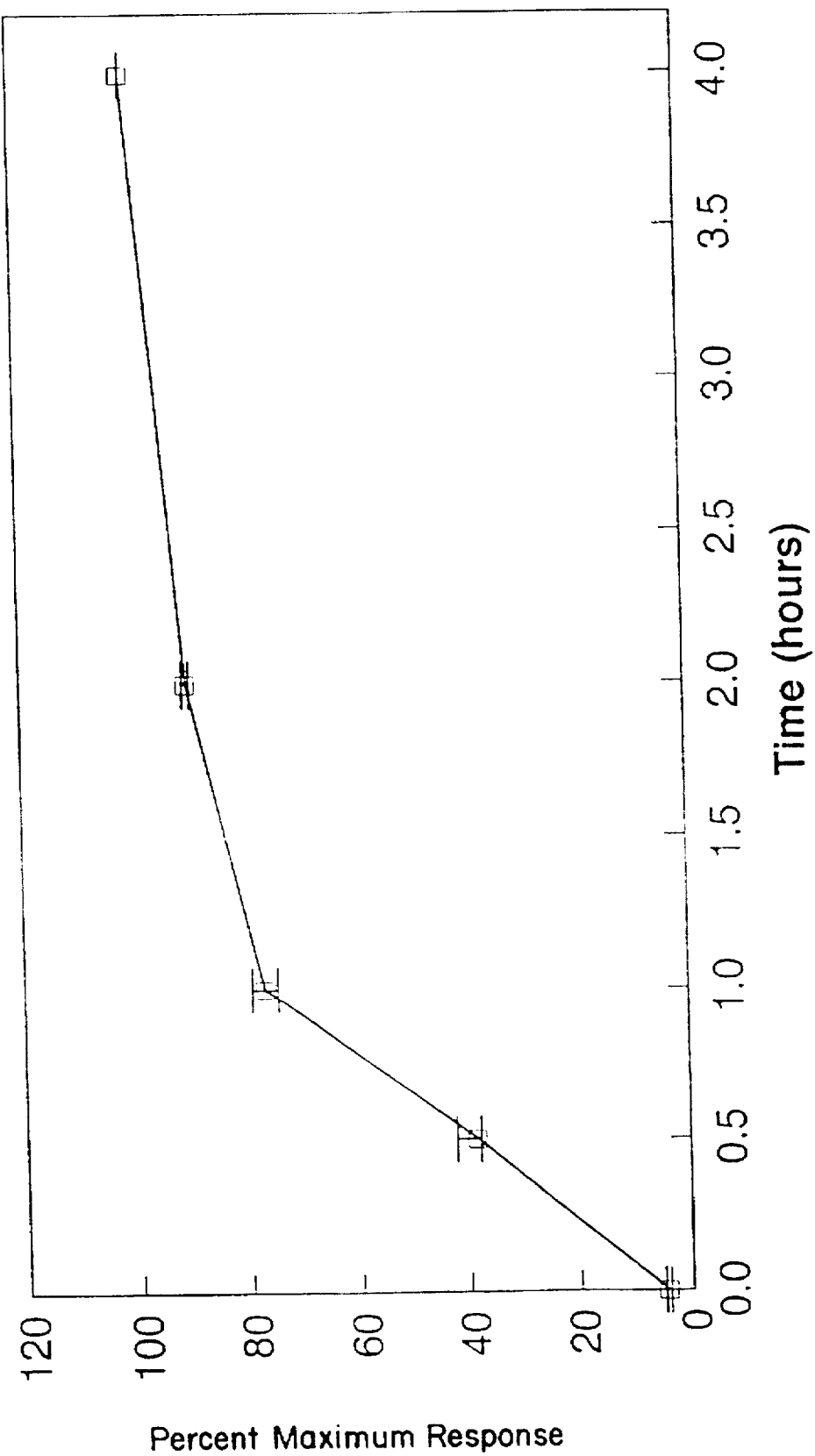

FIG. 15 shows the effect of varying incubation time with 1A3-HRPO conjugate on reactivity on an amniotic fluid pool.

Figure 16:
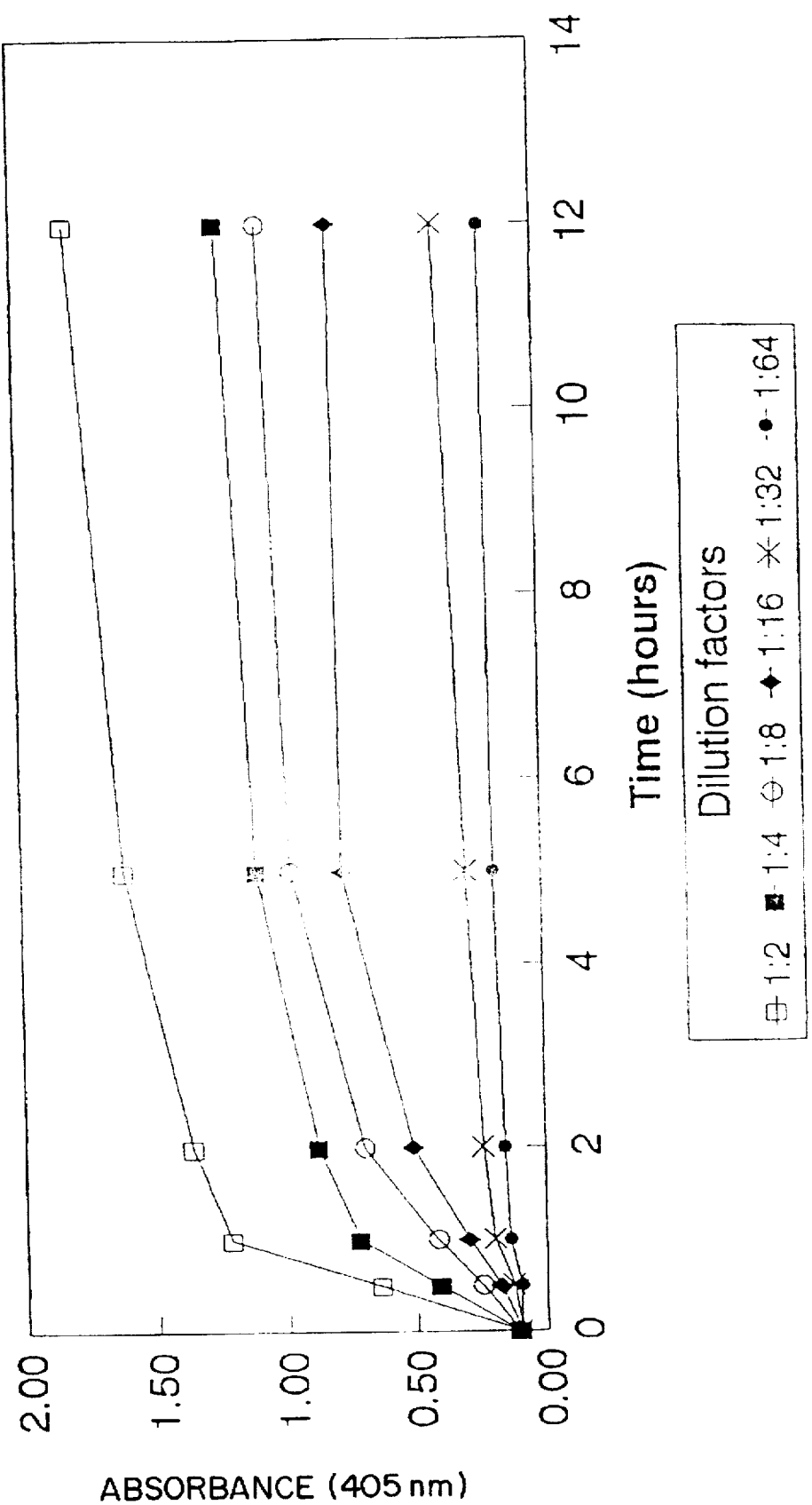

FIG. 16 shows the effect of varying incubation time with HRPO substrate on the reactivity of different dilutions of an amniotic fluid pool.

Figure 17:
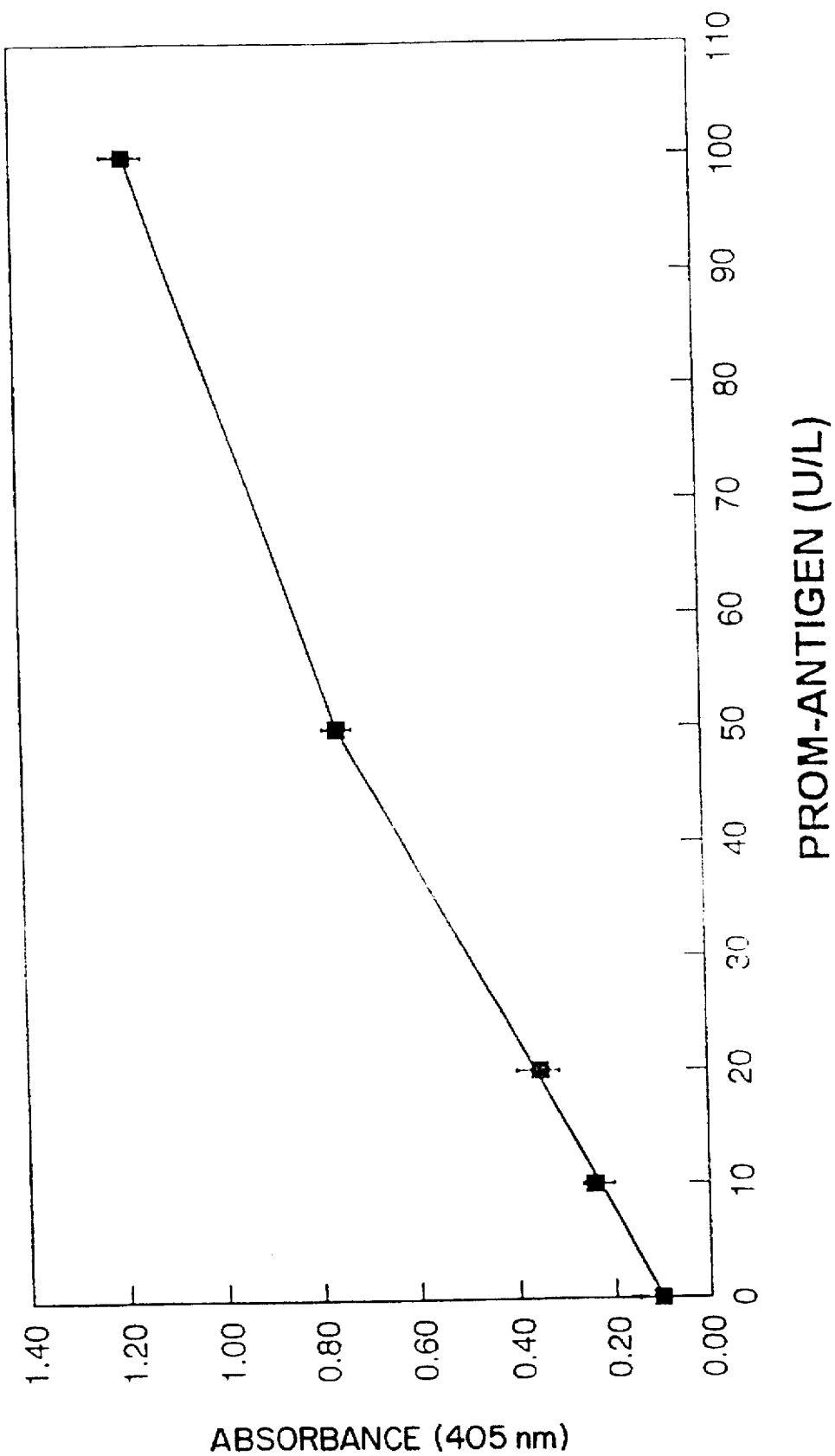

FIG. 17 is a typical standard curve obtained with the optimized ELISA procedure.

Figure 18:
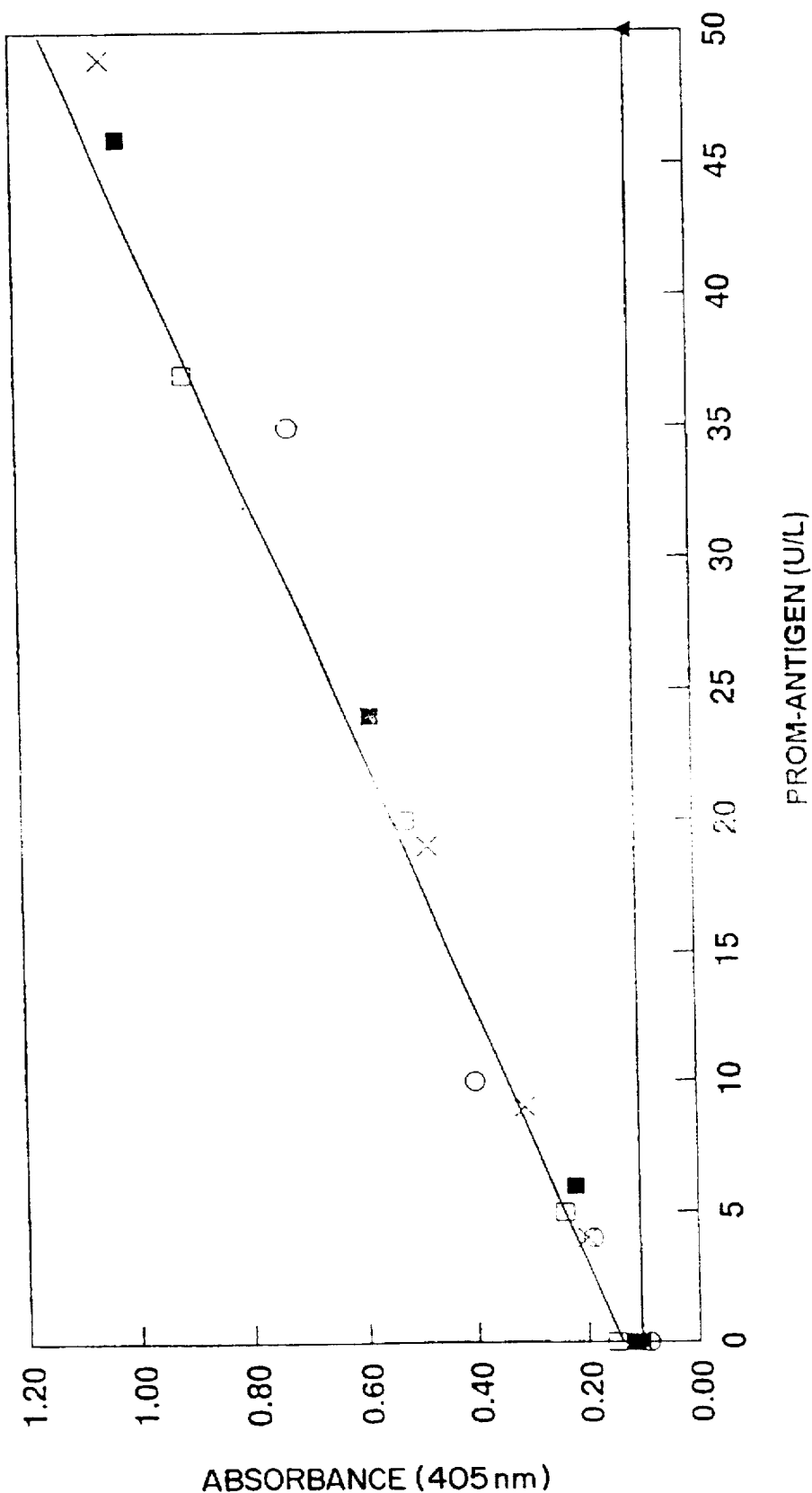

FIG. 18 shows dilution of three individual term amniotic fluids compared with the standard curve.

Figure 19:
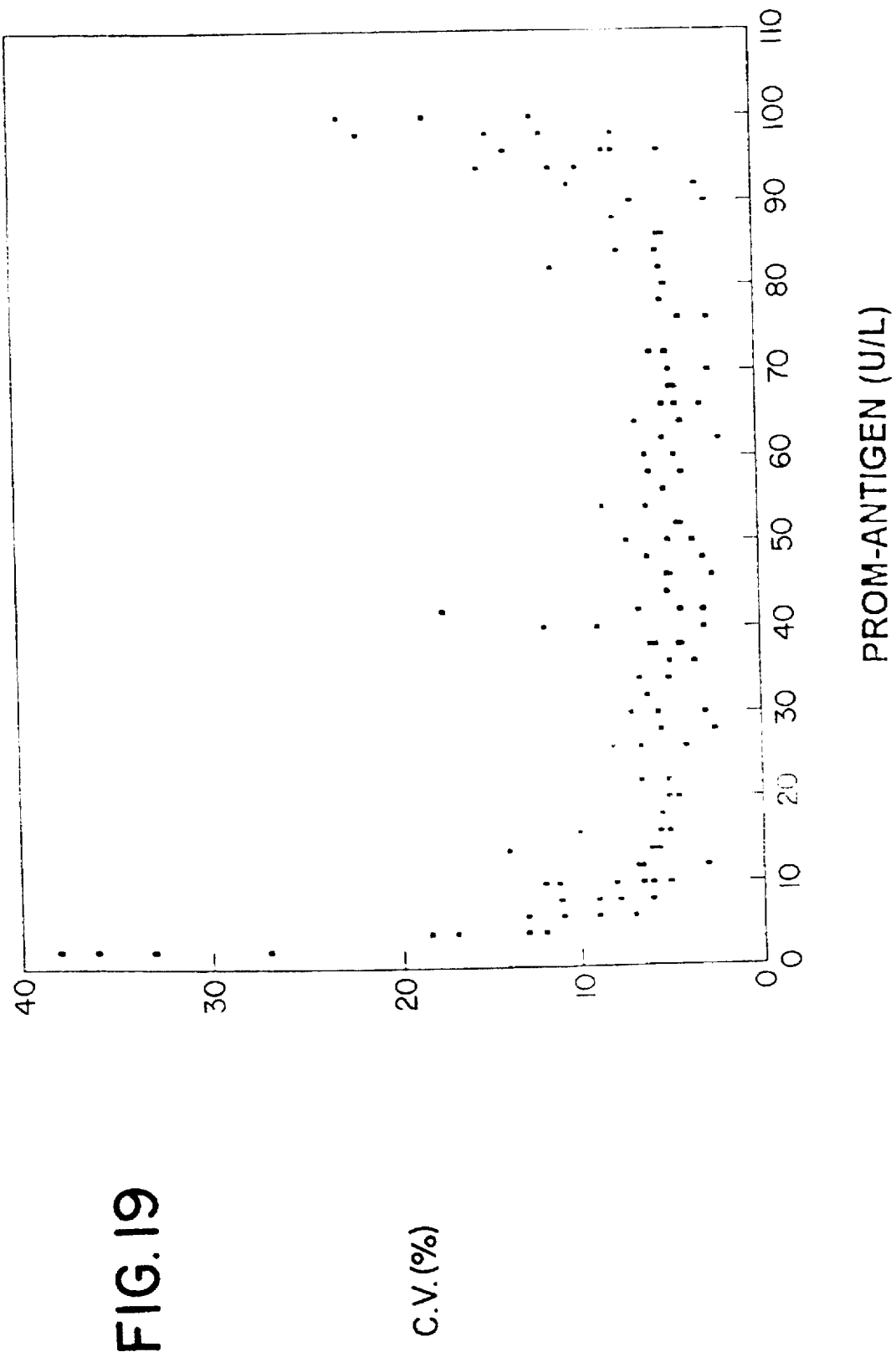

FIG. 19 illustrates the precision profile of 120 vaginal fluid specimens. CV is calculated from duplicates as the difference×100/mean.

Figure 20:
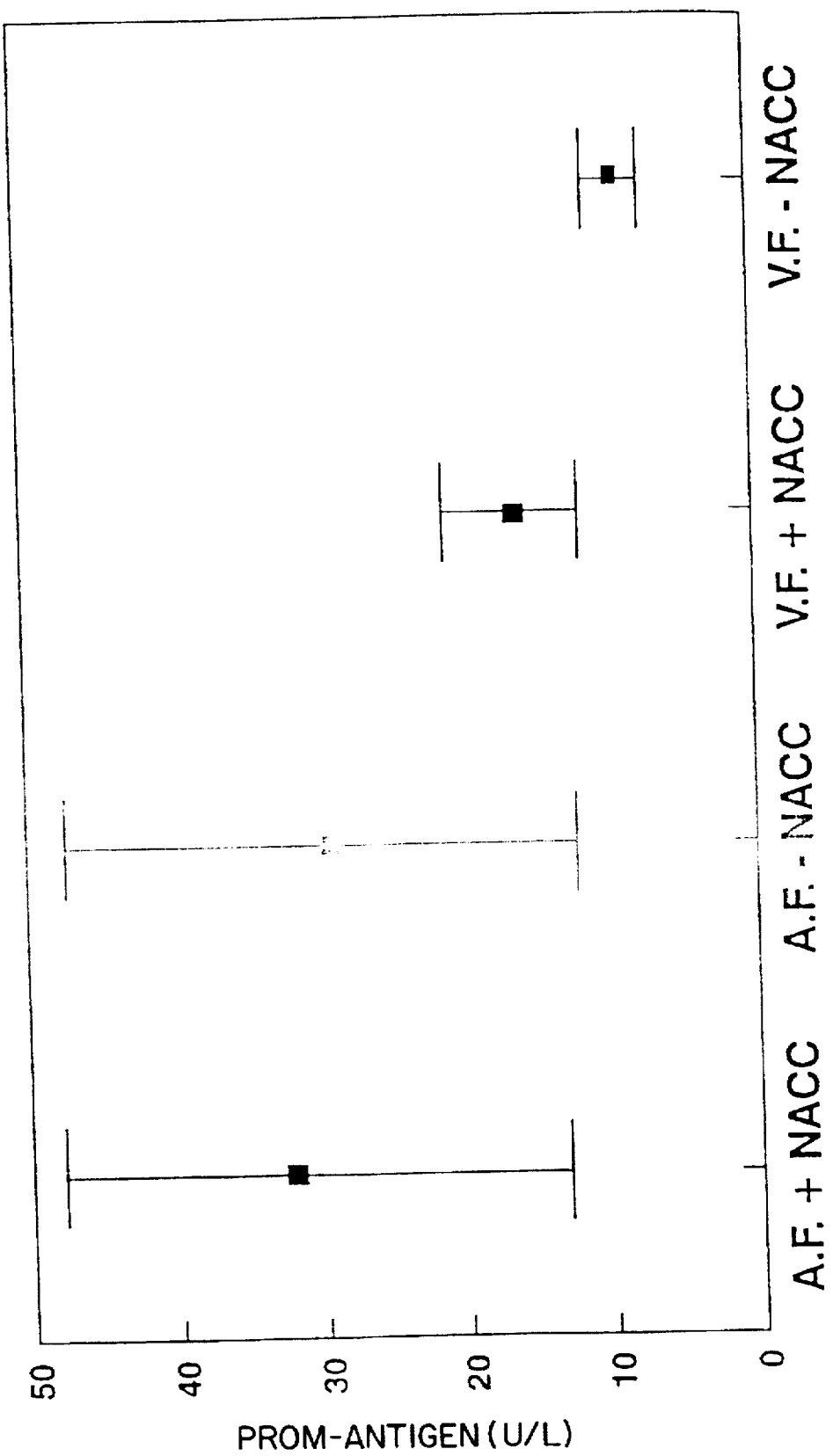

FIG. 20 shows the effect of pre-incubation with N-Acetyl cysteine on PROM antigen levels in 40 amniotic fluids.

A.F. Amniotic Fluid

N-ACC N-Acetylcysteine

V.F. Vaginal Fluid

FIG. 21 shows the reference range of PROM antigen levels in 1st, 2nd and 3rd trimester amniotic fluid.

A DETAILED DESCRIPTION OF THE INVENTION

METHOD

Purification of an amniotic fluid protein

Term amniotic fluid specimens surplus to requirements for L/S (Lecithin-Sphingomyelin) ration evaluation and unmatched random maternal sera were obtained from the Mater Miseriocordiae Hospital in Brisbane, Australia. 2 mL samples of 50 random term amniotic fluids and 50 unmatched maternal sera were each bought to 50% saturation with ammonium sulphate, mixed end-over-end for one hour at room temperature, and then ultracentrifuged at 10,000 g for 30 min on a Bechman Ultracentrifuge L8-M. The precipitate or pellet was resuspended in 5.1 mL 0.02M $K_2HPO_4$, pH 8.0 and the resulting solution (5 mL) was directly applied to a DEAE Affi-Gel Blue column (10 mL([BIORAD]) packed into a syringe and which had been equilibrated with ten column volumes of 0.02M $K_2HPO_4$, pH 8.0. The columns were washed with 50 mL of the same buffer and the bound fraction eluted with a linear gradient of 0.02–0.8M $K_2HPO_4$, pH 8.0. Unbound and bound fractions (10 mL) were collected and the columns were regenerated with 5 bed volumes of 2.0M NaCl in 0.02M $K_2HPO_4$, pH 8.0.

The fractions from the individual sample runs were analysed for protein subunit composition by SDS-PAGE according to the method of Laemmli (Nature 227:680 (1970)) with a vertical slab gel apparatus (BIORAD). Individual fractions (50 µL) were mixed with 200 µL sample buffer (20% glycerol (v/v), 2% (w/v) SDS, 5% (v/v) 2 β-mercaptoethanol, 0.00125% (w/v) bromophenol blue and 12.5% (v/v) 0.5M Tris-HCl, pH 6.8), boiled for 10 min at 100° C., and 10 µL aliquots were applied to the gel together with pre-stained molecular weight standards (BIORAD). Electrophoresis was performed in 10–24% and 4–15% linear gradient gels equilibrated with running buffer (125 mM Tris,0.96M glycine pH 8.0 containing 0.5% SDS (w/v)); proteins were visualised using a silver stain. All fractions from the first ten amniotic fluid and three maternal serum specimens were analysed by SDS-PAGE. Those fractions from ten amniotic fluids containing a protein (M.W. approx. 55,000 Da) which was absent from all maternal sera were then collected and analysed in subsequent specimens. In this regard it was noted that the bound fractions did not contain this protein. These fractions were individually concentrated 10-fold using a stirred cell with a YM-10 membrane and then chromatographed on a Sephacryl S-200 (Pharmacia) column (2.5 cm×75 cm) equilibrated with 50 mM Tris-HCl pH 7.2. Fractions (5 mL) were collected, incubated with SDS/nercaptoethanol as previously described; and examined by SDS-PAGE on a 12.5% homogeneous gel equilibrated with running buffer followed by visualisation with silver stain. Fractions containing the protein of interest which had an apparent molecular weight of 330,000 daltons from ten separate runs were pooled and concentrated with a stirred cell to a protein concentration of 1 mg/mL and used in the immunization protocol. This fraction contained predominantly the protein of interest, designated the PROM-Ag, and was used as the immunogen for antibody production.

Monoclonal antibody production and screening immunoassay

For primary immunisations of six BALB/c mice, 0.10–0.15 mg of PROM-Ag was emulsified in complete Freund's adjuvant (1:1 v/v) and injected subcutaneoulsy into each mouse. Booster immunisations with 0.10–0.15 mg antigen prepared with incomplete Freund's adjuvant (1:1 v/v) were given by the same routes. The initial boost with antigen was given at six weeks post-immunisation with subsequent boosts prescribed at two-weekly intervals for 8 weeks. Antibody levels were monitored by collecting eye bleeds, 6 weeks post primary immunisation and then weekly until 13 weeks on immunised mice, and evaluating the serum by an indirect one-site enzyme immunoassay.

In the indirect one-site enzyme immunoassay procedure, 100 µL antigen (0.2 mg/mL) in Tris-HCl buffer pH 7.2 was added to each well of 96-well microtitre plates (NUNC Immunoplate) and incubated at room temperature (approx. 25 ° C.) for one hour. The plate was washed three times with PBS [(Low Salt) L/S] Tween (136 mM NaCl; 3.2 mM $Na_2HPO_4$; 1.5 mM $KH_2PO_4$; 2.7 mM KCl containing 0.2% (v/v) Tween-20) and blocked with 0.1 mL/well PBS (L/S) Tween containing 100 mM L-lysine and 0.5% BSA for 2 hr at room temperature. Plates were washed 3 times with PBS(L/S)Tween, and 0.10 mL of mouse sera was then added to each well; blanks were similarly prepared but using 0.10 mL/well of sera collected from non-immunised BALB/c mice. After incubation at room temperature for one hour, plates were washed three times with wash buffer and 0.05 mL/well of peroxidase conjugated goat anti-mouse IgG diluted 1:1,000 in PBS/Tween was added and incubated for a further hour at room temperature. Following a further four washes, 0.10 mL/well of ABTS substrate solution (5 mM citric acid; 5 mM tri-sodium citrate; 0.4 mM azinobis [3-ethylbenzthiazoline sulfonic acid] diammonium salt activated with 0.003% (v/v peroxide) was added and the reaction allowed to proceed for 30 min. The reaction was stopped with 0.05 mL/well of 3.9% oxalic acid and the absorbance was measured in a Wellcozyme plate reader (Wellcome Diagnositics) at 405 nm.

One mouse was chosen for further treatment (see Results) and given a final subcutaneous boost of the same dose of antigen. Three days later, the mouse was sacrificed by $CO_2$ asphyxiation and the spleen was removed under sterile conditions and placed in a 60 mm petri dish (FLOW) in RPMI-1640 culture medium (FLOW). The spleen was perfused with medium by injecting it with a 26-gauge needle at five sites, thereby forcing medium into the spleen to release the cells. The cells were transferred to a sterile centrifuge tube, centrifuged (250×g for 10 min) and the supernatant removed. The cells were resuspended in 10 mL culture medium and counted on the Coulter Counter (Coulter). $1 \times 10^7$ NS1 cells grown in RPMI-1640/ 10% FCS were similarly centrifuged and resuspended in 10 mL RPMI-1640 and counted. Splenic lymphocytes were fused with NS1 myeloma cells at a ratio of 10:1 using 50% PEG 4000 in RPMI-1640. Hybrids were grown in a selection medium containing HAT (10 mM hypoxanthine; 0.04 mM aminopterin; 1.6 mM thymidine) $2 \times 10^5$ feeder cells/mL, 10% FCS, 100 U/mL penicillin, 50 U/mL streptomycin and 50 U/mL gentamycin in RPMI-1640 (Goding, 1986). 136 hybrids were obtained. Five clones secretin PROM-Ag antibodies were detected by indirect one-site enzyme immunoassay as described above. These hybrids were cloned three times by limited dilution. Clone 1A3/42 was grown as ascitic tumours in ten BALB/c mice; mice were injected with 0.5 mL pristane (SIGMA) intraperitoneally one week prior to injecting 1 mL of $2 \times 10^5$/mL hybridoma cells prepared in RPMI-1640. Tumour formation was observed in five of the mice three weeks post-injection. Ascitic fluid was collected in each case mouse after insertion of an 18-gauge needle into the peritoneal cavity of the $CO_2$ asphyxiated mice and drawing out the fluid. A total of 8 mL of ascitic fluid was collected from five mice.

Purification of monoclonal antibody

Ascitic fluid was dilipidated by addition of lipoclean (Behring). Lipoclean was added to ascitic fluid in a ratio of 3:2 (v/v), mixed and stored at 4° C. for 30 min. The solution was then centrifuged at 2500 rpm for 10 min and the aqueous fraction containing the antibody was collected, and stored at −70° C. until required.

To purify the monoclonal antibody from dilapidated ascitic fluid, a 100 mL hydroxyapatite (BIORAD) column (2.5 cm×20 cm) was prepared and equilibrated with 10 column volumes of 50 mM sodium phosphate buffer (pH 7.0). 5 mL of delipidated ascitic fluid was applied to the column and the unbound material washed through with 5 column volumes of 50 mM sodium phosphate buffer (pH 7.0). The immunoglobulin fraction was eluted using a linear gradient of 50–500 mM sodium phosphate buffer (pH 7.0) and 5 mL fractions were collected.

The purification of immunoglobulin was monitored by agarose gel electrophoresis performed on a Helena electrophoresis unit. Samples (5.0 µL) were applied at the cathode end of the Titan HRE agarose gels (HELENA) and subjected to electrophoresis for 25–30 min 50 mM barbital buffer pH 8.6 for with a 100 V direct current potential. The proteins were fixed in 10% TCA for 10 min, and the gel dried and stained with 0.1% Coomassie Blue R in 20% methanol/10% acetic acid. The gel was destained in 20% methanol, 10% acetic acid.

The antibody was recovered in fractions 29–34 (see FIG. 4) and pooled to give 30 mL antibody solution, containing 0.63 mg/mL protein. This solution was concentrated 10-fold using a stirred cell with a 10,000 M.W. cut-off membrane and stored in 0.2 mL aliquots at −70° C. The antibody was adjusted to 35 µg/mL with 100 mM sodium phosphate buffer, pH 5.0, prior to use for coating the plate wells for ELISA. Some of the purified IgG was adjusted to 2 mg/mL using 10 mM sodium carbonate buffer pH 9.6 and dialysed overnight at 4° C. against the same buffer prior to conjugation with horse radish peroxidase (HRPO [SIGMA]).

IgG conjugation with Horse Radish Peroxidase (HRPO)

The method used was based on that described by Nakane, P. K., et al. (J. Histochem. Cytochem. 22:1084 (1974)).

5 mg of horse radish peroxidase was dissolved in 1.0 mL distilled water. Sodium periodate (0.2 mL of 0.1M) was added to activate the HRPO, this being mixed in the dark at room temperature for 30 min, and then dialysed overnight at 4° C. in the dark with 5.0 L of 1.0 mM sodium acetate buffer pH 4.4. The dialysed activated periodate-HRPO solution was adjusted to pH 9.6 with 200 mM sodium carbonate buffer. Antibody solution (3.5 mL; 2 mg/mL in sodium carbonate buffer pH 9.6) was mixed with HRPO (1.15 mL; 2.02 mg/mL in 1 mM acetate buffer pH 4.4) to give a ratio of 4.0 mg IgG: 1.0 mg HRPO aldehyde and mixed at 20 rpm at room temperature in the dark for 2 hr. Sodium borohydride solution (0.1 mL; 4.0 mg/mL) was then added to the solution, followed by standing for 2 hr at 4° C. The solution (8.25 mL) was then loaded onto a Biogel A-0.5 m column (2.5 cm×20 cm) pre-equilibrated with 10 column volumes of PBS (136 mM Nacl, 2.7 mM KCl, 3.2 mM $NA_2HPO_4$, 1.5 mM $KH_2, PO_4$, pH 7.4). A R-Z ratio value was performed on the colored fractions; fractions 4–8 demonstrated an R-Z value between 0.25–0.6 (Table 3) and were pooled and stored at 4° C. in the presence of 0.1% thimerosal. This pool was diluted with PBS/Tween wash buffer to varying concentrations (range 50–1000 fold) to find the optimum concentration for use (150-fold) as the conjugate in the ELISA procedure.

Characterization of the reactivity of Monoclonal Antibody (Clone 1A3) SDS-PAGE studies of Amniotic Fluid Amniotic fluid samples (15 µL of 0.02 mg protein/mL) in 45 µL sample buffer (20% glycerol (v/v), 2% (w/v) SDS, 5% (v/v) 2-β-mercaptoethanol, 0.00125% (w/v) bromophenol blue and 12.5% (v/v) 0.5M Tris-HCl, pH 6.8) were boiled for 10 minutes. SDS-polyacrylamide gel electrophoresis was performed on 7.5 and 12% gels according to the procedure of Laemmli, U. K., (Nature 227:680 (1970)). Calibration curves for molecular weight estimation were obtained from pre-stained standards (BIORAD) transferred to the membrane. Electrophoresis was performed on the Mini Protean II system (BIORAD) for 60 min at 180 V. Western blotting was performed according to the method of Towbin (1984) with some modifications; i.e. the use of Hybond membrane (AMERSHAM) and 48 mM Tris, 39 mM glycine, Ph 9.2 containing 20% (v/v) methanol as a blotting buffer. Electrophoretic transfer was performed at 15 V for 45 min using a Trans-Blot Electrophoretic Transfer Cell (BIORAD). Blots were soaked in 10 mM Tris,. 0.9% NaCl (w/v), 100 mM L-lysine, 0.5% BSA (w/v) for 2 hr at room temperature and then washed in 3×10 min consecutive washes in 10 mM Tris, 0.9% NaCl (w/v) and 0.02% Tween-20 (v/v). The conjugate, diluted in the same buffer (1/100), was added to the blot and left overnight at 4° C. Blots were rinsed as before and incubated with substrate, DAB (3,3'-diaminobenzidine tetrahydrochloride) prepared in 50 mM Tris-HCl, pH 7.6 containing 0.02% ($H_2O_2$) for 30 min; followed by termination of the reaction by placing the blot into distilled water.

Isoelectric Focusing

Isoelectric focusing was performed on 1% agarose gels prepared with 3% sucrose and 2% Biolyte (v/v) 3.5–9.5 (BIORAD). Gels were pre-focused for 1 hr at 5 W, 1500 V, 150 mA with 1M NaOH (cathode) and 0.005M $H_2SO_4$ (anode) buffers. Samples of amniotic fluid purified by Sephacryl S-200 column chromatography, and IEF standards (BIORAD) were applied to the gel on filter paper strips and focused for a further 2 hr. Proteins were transferred onto Hybond by placing the gel onto the surface and placing a weight onto the gel for 15 min. The antigen was detected on the blot by the procedure described for SDS-PAGE. The gel was stained for protein by initially drying the gel, fixing for 20 min using 35% methanol, 13% tricarboxylic acid, 3.5% sulfosalicylic acid, washing the gel in 30% methanol, 10% acetic acid and staining in Coomassie blue (0.2% w/v). The gel was destained in 30% methanol, 10% acetic acid.

Gel Permeation Chromatography

A column (2.5 cm×100 cm) was packed with Sephacryl S-200 and equilibrated at 1.0 mL/min with 20 mM Tris-HCl (pH 7.0) for 12 hr. Following column equilibration (10 column volumes), gel filtration standards (BIORAD) were run and a standard curve constructed. Amniotic fluid (50 mL) was dialysed at 4° C. against three 5.0 L changes of 20 mM Tris-HCl pH 7.0 and concentrated 20-fold on a stirred cell with a 10,000 MW cut-off membrane (Amicon). 2 mL of concentrated amniotic fluid, spiked with Dextran Blue-2000 [(Pharmacia) 1% v/v], was added to the column and 5 mL fractions collected. Fractions were screened by the two-site ELISA; the native molecular weight was determined from the standard curve for fractions positive by ELISA.

ELISA Protocol

Nunc plates were activated for 4 hr at room temperature with 0.2 mL/well 0.2% glutaraldehyde prepared in 100 mM sodium phosphate buffer pH 5.0. The plates were washed three times in 100 mM sodium phosphate buffer pH 5.0 and incubated with 0.1 mL/well purified immunoglobulin (35 μg/mL in 50 mM sodium phosphate buffer pH 8.0) at 4° C. overnight. Plates were washed three times in 0.9% NaCl and 0.1 mL per well of 100 mM lysine, 0.5% BSA, 0.02% azide was added and stored at 4° C. for up to 14 days prior to use.

Before use, the immunoglobulin coupled plates were washed three times in PBS [(high salt)HS]/Tween wash buffer (3.2 mM $Na_2HPO_4$, 1.5 mM $KH_2PO_4$, 2.7 mM KCl, 272 mM NaCl, pH 7.4 containing 0.5% (v/v) Tween 20), followed by addition of the same buffer (25 μL per well) prior to sample application. 15 term amniotic fluids were pooled and serially-diluted ½–1/128 with PBS (HS)/Tween to allow the production of a standard curve. The concentration of the pool was given an arbitrary value of 100 U/L COVO Antigen. To perform the assay, samples and standards were applied (0.1 mL/well) in duplicate and incubated at room temperature for 2 hr. Blanks containing PBS (HS)/Tween (0.1 mL/well) instead of sample, were also included. An amniotic fluid control was prepared from 20 random term amniotic fluids and run on every plate. After a further three washes in PBS (HS)/Tween, 50 μL IgG-HRPO conjugate was added to each well, and incubated at room temperature for 1 hr. After four washes with PBS (HS)/T, 0.1 mL of ABTS solution was allowed to react with the enzyme for 1 hr. The reaction was stopped with 3.9% oxalic acid (50 μL per well). Optical densities of samples (OD sample) were measured at a wavelength of 405 nm. Calibration curves were constructed from the amniotic fluid pool after subtraction of blank values (OD blank). The levels of antigen in individual specimens and controls were calculated from the standard curve.

Selection of Patients for Establishing PROM Antigen Reference Range

To establish the normal reference range, the PROM antigen level was measured in post-rupture of the membrane specimens (post-ROM) obtained from the following group of patients:

(a) 50 amniotic fluid specimens from each trimester of pregnancy were collected by amniocentesis performed for various obstetric indications.

(b) 40 amniotic fluid specimens were collected at Caesarean section (CS) by aspiration of 2 mL of liquor with a syringe.

(c) 70 specimens were collected from women after artificial rupture of membranes (ARM), where fluid loss was observed during the procedure, and a sample of liquor of 2 mL was able to be aspirated with a syringe.

(d) A further 50 vaginal specimens were collected from women who gave a history of spontaneous rupture of the membranes (SRM), and in whom a pool of liquor was observed in the vagina, from which a sample of 2 mL could be aspirated with a syringe.

Similarly, PROM antigen levels were measured in specimens of vaginal fluid collected from 50 women with intact membranes in the Labour Ward prior to artificial rupture of the membranes (pre-ROM). The specimens were regarded as negative controls if the women gave no history of fluid loss and liquor was not evident on clinical examination.

Method used for obtaining the vaginal specimens is described below in the section "Procedure for Vaginal Fluid Collection".

PROM antigen levels were also measured in the sera obtained from 500 pregnant women who had blood samples collected routinely during pregnancy.

Procedure for Vaginal Fluid Collection

After advising the patient of the procedure, a vaginal speculum examination was performed and the posterior fornix was visualised. If fluid was present in the vagina, it was aspirated with a 2 mL syringe fitted with an aspiration cannula. Where fluid was not observed, the external cervical os was washed with 2 mL sterile saline and the fluid was then aspirated from the posterior fornix. Specimens were placed in sterile sample tubes and transported to the Laboratory where they were frozen at −70° C. until analysis.

Interfering Substances

A variety of substances were tested for potential interference in the assay procedure by diluting them 1:1 with an amniotic fluid pool. The amniotic fluid pool had a PROM antigen level of 36 U/L and gave a level of 18 U/L when diluted 1:1 with PBS (H/S)/Tween. Selection of Specimens in Two "Blinded" Studies Pre- and post-ROM (rupture of membrane) specimens of fluid were collected for analysis by an obstetrician from two separate groups of patients whose names were withheld from the Research staff and who were identified to them only by a randomly allocated number. In the first "blinded" group (Study A), specimens were obtained from six pregnant women who were booked for elective CS. Immediately prior to the CS, vaginal fluid specimens were obtained, as described under "Procedure for vaginal fluid collection". At CS, amniotic fluid was aspirated through intact membranes into a sterile syringe. Each specimen was numbered and sent to the Laboratory for analysis. Because there were two sets of triplets in the group, there were 10 post-ROM specimens.

In the second "blinded" study (Study B), 46 vaginal specimens of which 21 were pre-ROM and 25 post-ROM collected as previously described. Pre-ROM and post-ROM specimens were obtained from the same patients in 14 women (28 specimens) and the other 7 pre- and 11 post-ARM were collected from different women.

RESULTS

Identification and Purification of an Amniotic Fluid Protein

Figure 1:
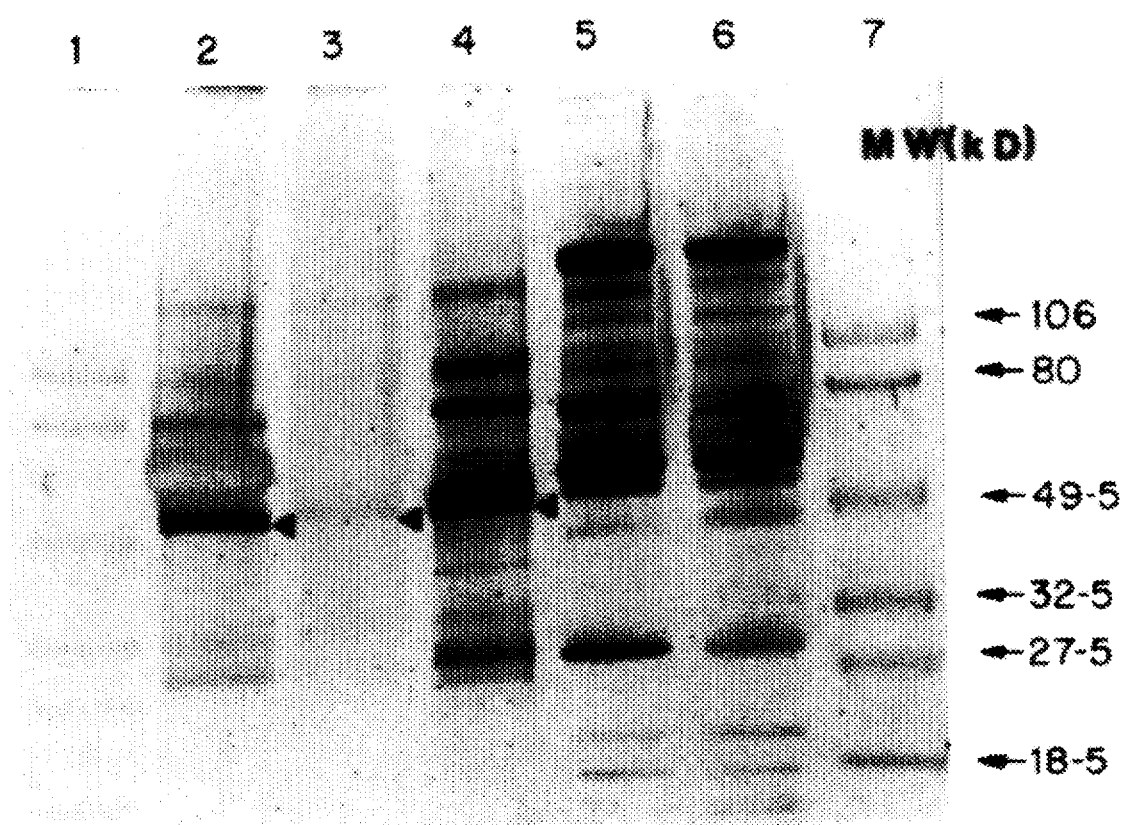
FIG. 1 illustrates typical protein patterns obtained by SDS-PAGE electrophoresis of native amniotic fluid protein and amniotic fluid and maternal serum supernatants post ammonium sulphate precipitation. Amniotic fluid proteins are denatured with SDS/mercaptoethanol during the purification of PROM antigen (see arrows) on 4–15% SDS-PAGE gradient gels.

We processed 50 term amniotic fluid specimens and 50 random unmatched maternal sera individually in order to identify a protein uniquely present in the amniotic fluid specimens. The initial 50% ammonium sulphate treatment resulted in the precipitation of 40 (±2.1) % of serum protein and 80 (±4.7) % of amniotic fluid protein (Table 1). Typical protein patterns by SDS-PAGE electrophoresis of native amniotic fluid and amniotic fluid and maternal serum supernatants post ammonium sulphate precipitation are shown in FIG. 1. Amniotic fluid, pre- and post-precipitation, shows a prominent band of sub-unit molecular weight 55,000 (±2,000) daltons (Da) which is not seen in maternal sera. This band was present in all 50 amniotic fluid specimens but was not seen in any maternal sera. Maternal serum specimens were not further processed due to the apparent absence of this protein, subsequently called the PROM-Ag.

Amniotic fluid supernatants (5 mL) were individually subjected to chromatography in 100 mL volume DEAE Affi-Gel Blue columns and serial 10 mL fractions were collected. These fractions were subjected to SDS-PAGE electrophoresis and fractions 4–10 were found to contain the PROM-Ag. These fractions were pooled and contained 1.4 mg of protein (Table 1). A typical SDS-PAGE result for this pool can be seen in FIG. 1, lane 5.

The post-Affi-Gel Blue pools containing the antigen were concentrated 20-fold to 2.5 mL and individually applied to a pre-calibrated (2.5×7.5 cm) Sephacryl S-200 column.

Serial 5 mL fractions were collected and subjected to SDS-PAGE electrophoresis to identify the protein at 55,000 Da. Fractions corresponding to molecular weight range of 310,000–350,000 Da were found to contain the protein giving an estimated native molecular weight of 330,000 Da. The sub-unit molecular weight from SDS-PAGE electrophoresis of 55,000 Da is consistent therefore with the native protein being a hexamer. Fractions containing the protein were pooled, yield 0.36 mg of protein (Table 1). A typical SDS-PAGE result is shown in FIG. 2 which demonstrates that the protein is substantially pure with minor contaminants at sub-unit molecular weights of 82,000 and 30,000 Da, and one major contaminant of 57,000 Da.

These preparations from the 10 unrelated fluid specimens were now pooled, concentrated in a stirred cell to a final protein concentration of 1 mg/mL and used for immunization of BALB/c mice.

Monoclonal Antibody Production

Six BALB/c mice were immunized with PROM-Ag and were test bed on seven occasions from 6–15 weeks. These sera were tested for immunoreactivity to amniotic fluid using a one-site ELISA technique and compared with sera from non-immune BALB/c mice. These results are shown in Table 2. Two mice (#1,3) showed no immune response when assayed in this manner, three mice (#2,4,5) showed a partial response and one mouse (#6) demonstrated a 5-fold increase over the blank absorbance. This latter mouse was sacrificed and the spleen cells were fused with NS1 myeloma cells.

We obtained 136 hybrids from this fusion. All the culture supernatants from these hybrids were tested for reactivity, by an indirect one-site ELISA, against amniotic fluid and maternal serum pools (Table 3). Five hybrids reacted with amniotic fluid alone, 96 reacted with both fluids and 17 with neither. Hybrids 1A3/42, 11B6/68, 2C5/48, 2C6/86 and 12D2/77; which reacted with amniotic fluid alone were cloned three times by limited dilution and retested for reactivity with amniotic fluid and maternal serum (FIG. 3). Cell line 1A3/42 was selected for further analysis, and lines 11B6/68, 2C5/48, 2C6/86 and 12D2/77 were selected for storage in liquid nitrogen.

Characterization of Monoclonal Antibody 1A3

Clone 1A3/42 wa propagated in the peritoneal cavities of 12 BALB/c mice. Ascitic fluid collection developed in seven of these mice after three weeks. 10 mL of ascitic fluid was obtained from the seven mice, delipidated and subjected to hydroxylapatite chromatography (FIG. 4). Individual fractions were screened for reactivity to amniotic fluid by a one-site ELISA (FIG. 4). This procedure substantially separated the gamma globulin fraction which proved to have as expected a major monoclonal band in the gamma region when analysed by agarose gel electrophoresis (FIG. 5). 35 mL of purified immunoglobulin from the hydroxylapatite column was obtained containing 0.62 mg/mL protein which was substantially pure monoclonal antibody (FIG. 5).

This monoclonal antibody preparation was used both as a capture and, following conjugation with horseradish peroxidase, as the conjugate in the subsequent two-site ELISA assays. The conjugate was also used as a specific staining reagent to characterize the corresponding amniotic fluid protein by western blot analysis, and to test its identity to the original antigen purified from amniotic fluid.

FIG. 6a shows the results in a western blot analysis following SDS-PAGE electrophoresis in 4–15% gradient gels in the presence of SDS/mercaptoethanol. Only one band of reactivity is seen and it is identical in three randomly selected term amniotic fluids. This band corresponds to a sub-unit molecular weight of 55,000±2,000 Da (FIG. 6b), a mass identical to that of the protein originally purified from amniotic fluid.

The isoelectric point of the protein was also determined by western blot analysis (using monoclonal 1A3-HRPO conjugate) following isoelectric focusing in an agarose gel, using ampholines with a pH rage from 3–10. We used both purified protein and one native random term amniotic fluid for this analysis. The results are shown in FIG. 7a. Only one major band of reactivity against purified protein is evident (FIG. 7a) which corresponds to an isoelectric point of 4.9 (FIG. 7b).

The native molecular weight of the protein was determined by testing the reactivity of fractions eluted from a pre-calibrated Sephacryl S-200 column (FIG. 8a) using a two-site ELISA (a description of this assay follows). This assay uses monoclonal 1A3 as both the capture antibody and conjugate. The results are shown in FIG. 8b. 2 mL of post DEAE Affi-Gel Blue amniotic fluid was loaded onto the column. Fractions 17–18, which corresponded to a molecular weight of 330,000±10,000 Da, reacted positively in the ELISA test (FIG. 8c). No other fractions were found to show reactivity. This native molecular weight corresponds with that found previously, during initial protein purification, and is consistent with monoclonal antibody 1A3 reacting with the antigen that was originally purified.

Development and Optimisation of a two-site Direct ELISA Assay for Amniotic Fluid Protein (PROM-AQ) based on Mohoclonal 1A3 Optimiisation of ELISA Assay It was considered necessary to develop a two-site ELISA assay for the protein (PROM-Ag), which would allow for rapid and sensitive assay of this protein, but which would be reagent-economical at the same time.

We pooled 50 amniotic fluids for use as a standard in the assay. This amniotic fluid pool was assigned a concentration of 100 U/L PROM-Ag. Randomly selected term amniotic fluids and maternal sera were used as specimens.

In FIG. 9 is shown the effect of varying the concentration of capture antibody used to coat the plates. Response is measured by the development of colour at 40 nm. The mean (SEM) of three amniotic fluid and three maternal serum specimens are shown. The maternal sera do not react at any concentration but the response of amniotic fluid reaches a maximum at 2.5 µg/well. A reduced response is seen at higher antibody concentrations possibly due to steric hindrance or cross-reactivity problems giving a lower antigen binding capacity. Demonstrating the use of a narrower concentration range of capture antibody with a maximal response at 1.75 µg/well; this concentration was chosen for use in the optimized assay procedure.

In FIG. 10 is shown the effect of different blocking agents used to suppress non-specific binding of non-specific proteins. Four reagents were compared: 100 mmol/L lysine, 0.5% (w/v) BSA in 100 mM sodium phosphate buffer pH 8.0, 100 mmol/L lysine in 100 mM sodium sulphate buffer pH 8.0; 5% (w/v) milk powder (Carnation Trim Milk Powder) in PBS and 1% (v/v) swine serum (GIBCO) in PBS. Serial dilutions (1:2, 1:5, 1:10 and 1:20) of the same pool of 10 amniotic fluids are compared. Blank wells contained sample buffer (PBS/Tween) only and were used to determine non-specific binding of antibody-HRPO conjugate to the well. The different blocking agents had little effect on the blank values but omission of BSA from the lysine solution, and the presence of swine serum and milk powder inhibited the binding of antigen when compared to the lysine/BSA blocking agent. Lysine/BSA was selected for use in the optimized procedure.

In FIG. 11 is shown the effect of serial dilutions of antibody-HRPO conjugate. Results are the mean (SEM) of five randomly selected amniotic fluid specimens. After an initial plateau, response falls exponentially at dilutions greater than 1/150 indicating that the amount of tag antibody is becoming rate-limiting. A dilution of 1/150 was selected for use in the optimized assay procedure.

In FIG. 12 is shown the effect on different sample diluents. Three reagents are compared: PBS/Tween-20, PBS and PBS/swine serum (1% [v/v]). Serial dilutions (1:2, 1:5, 1:10, 1:20 and 1:50) of the same pool of amniotic fluids are compared. Blank wells contain sample diluent only and are used to compare the effects of non-specific binding. The different sample diluents had little effect on the non-specific binding, but omission of Tween or addition of swine serum appeared to inhibit the binding of protein (PROM-Ag), when compared to the result using PBS/Tween reagent. PBS/Tween was selected for use in the optimized procedure.

In FIG. 13 is shown the effect of the pH of the sample diluent on non-specific binding and on antigen binding. PBS/Tween buffer at pH 2, 3, 4, 5, 6, 7 and 8 were prepared and used to dilute a pool of five amniotic fluids to 1:2, 1:4, 1:8, 1:16 and 1:32. Addition of buffer alone was used to assess non-specific binding. The pH appears to have little effect on non-specific binding. However, binding of the antigen is inhibited at acid pH presumably due to the masking of charged groups on the antigen or the antibody. This is less marked at low amniotic fluid dilutions probably due to the buffering effect of the amniotic fluid itself. We selected sample diluent buffer pH 7.0 for use in the assay procedure.

The effect of varying sample incubation time (0.5, 1, 2 and 4 hr) on the ELISA determination of three random term amniotic fluids was examined. Results are expressed as the percent of maximal response at 4 hr and are calculated as (Abs[405 nm])-reagent blank) at ×hrs/(Abs[405 nm]—reagent blank) at 4 hr. The results, shown in FIG. 14, show that 78 (0.76) % mean (SEM) of this nominated maximal binding was achieved at 1 hr. In order to perform the assay within one working day, a 1 hr incubation time was selected.

The effect of varying the incubation time with the antibody-HRPO conjugate from 0.5 to 1, 2 and 4 hr on three random term amniotic fluids. Results are expressed as the percent of maximal response at 4 hr and are calculated as (Abs[405 nm]—reagent blank) at ×hr (Abs[405 nm]—reagent blank) at 4 hr. The results in FIG. 15 show that binding of the conjugated antibody was 78 (0.89) mean (SEM) % of maximal binding by 1 hr. In order to perform the assay within one working day, an incubation time of 1 hr was selected.

The time course of colour development with ABTS color reagent from 0.5–12 hr on several dilutions of a pool of five random term amniotic fluid specimens (FIG. 16). Wells containing PBS/Tween instead of sample were used as the reagent blank.

Color development appeared rapid and linear for the first hour at all dilutions. The color development then slowed at all dilutions of sample and appeared independent of the concentration of 1A3-HRPO conjugate (dilution of 1:150 with PBS(high salt)/Tween in the well. These findings suggest that a substrate of the peroxidase reaction (possibly the peroxide) degrades spontaneously at a rate substantially faster than its rate of consumption in the color reaction and becomes rate limiting after 1 hr. We selected an incubation time of 1 hr for the color reaction to avoid this effect.

Evaluation of the Optimized ELISA Assay for PROM Antigen

The optimized procedure was evaluated to determine its precision, sensitivity and specificity for amniotic fluid. In FIG. 17 is shown a typical standard curve for this assay. Results are expressed as the mean (±SEM) of 10 replicates. The PROM antigen content of an undiluted pool of 50 amniotic fluids was assigned a PROM antigen level of 100 U/L. The standard curve shows a good correlation coefficient (r=0.992) with an absorbance of 1.22 (0.04) mean (SD) at a level of 100 U/L the mean concentration of protein found in normal amniotic fluid.

Serial dilutions of three individual fluids are shown in FIG. 18. These fluids show parallelism with the standard curve indicating that the antigen in the standards stored at −70° C. has not lost any immunological activity and is immunologically identical with that found in fresh amniotic fluid specimens.

A precision profile of 120 vaginal fluid specimens is shown in FIG. 19. The assay shows good precision between 20–90 U/L with a CV of duplicates of less than 10%.

The within-run precision was estimated from two pools analysed 50 times each. These pools gave values of 20 (1.2) mean (SD) and 50 (1.9) mean (SD) yielding Cv's of 4% and 2% respectively. The between-run precision was estimated from two pools run 10 times each in four different rows. These pools gave values of 19.8 (1.5) mean (SD) and 48.8 (2.2) mean (SD) yielding CV's of 7.5% and 4.5% respectively.

A variety of substances were tested for potential interference in the assay procedure by diluting them 1:1 with an amniotic fluid pool. The amniotic fluid pool had a PROM-Ag level of 18 U/L when diluted 1:1 with PBS/T. The results of the interference study are shown in Table 4.

Aliquots of 40 amniotic fluids, 20 maternal seras and 16 vaginal fluids were mixed with the mucolytic agent N-Acetylcystein [(NACC) (0.8% NACC in PBS (LS)/Tween/I M NaOH pH 7.0)] and pre-incubated at R.T. for 5 min prior to application to the ELISA plates. The results are shown in FIG. 20.

The NACC had no effect on PROM antigen levels in 40 term amniotic fluids showing that it did not inhibit the immunoreactivity of the PROM antigen. It was, however, active in lysing mucus as observed by visual inspection and enabled the detection of PROM antigen in 16 vaginal fluid specimens.

The reference range for PROM antigen in amniotic fluid was investigated on amniotic fluid specimens obtained at different gestational ages during pregnancy. The results are shown in FIG. 21. The level in the first trimester (26.5 (2.47) U/L) is significantly lower than that in the third trimester (30.2 (2.56) U/L). The levels during the second trimester (28.4 (2.03) U/L) were similar to those of the third trimester.

CLINICAL RESULTS

All the post-ROM specimens were associated with a level of PROM antigen >10 U/L.

In contrast, all the pre-ROM specimens and the maternal sera gave levels of ≦10 U/L. It was decided therefore that levels >10 U/L would be indicative of membrane rupture in clinical samples.

The results of pre- and post-CS-ROM study (Study A) are shown in Table 5. All specimens were correctly identified as being either pre- or post-ROM.

The results of the pre- and post-vaginal-ROM study (Study B) are shown in Table 6.

Initially, 39 of the 46 specimens (84.8%) were correctly identified as either pre- or post-ROM. The other seven specimens gave results at variance with the pre- or post-ROM expectations. Two of the seven (numbers 6 and 25, Table 6) from the pre-ROM group gave PROM antigen levels that were >10 U/L (false positives), and five (numbers 2, 4, 11, 18 and 30) in the post-ROM group gave PROM antigen levels that were <10 U/L (false negatives).

When the charts of the two mothers who gave false positive results were reviewed, it was apparent that the membranes in these women may have been ruptured. One woman (number 6) presented to the Labour Ward in established labour, with the cervix already 3 cm dilated and fully effaced, although the fore-waters were still found to be intact and the DAO test was negative. The other woman (number 15) also presented to the Labour Ward in early labour at 36 weeks gestation, and on ultrasound examination was noted to have a markedly decreased amniotic fluid volume. Caesarean section was performed shortly afterwards when the fetus became distressed, and at operation, the surgeon commented that there was "minimal liquor" within the uterus. The DAO test was also registered positive, thus providing further evidence that the membranes had been ruptured.

When the charts of the five women who gave false negative results were reviewed, there seemed little doubt that the membranes had been successfully ruptured at ARM. However, all these and a few other specimens were noted to contain a varying amount of mucus, which sometimes made them difficult to aspirate with a pipette, and it was postulated that the mucus might inhibit antigen migration from within the specimen to the capture antibody held at the base of the ELISA well.

To test this hypothesis, the use of N-Acetylcysteine (NACC) as a mucolytic agent was investigated. The results for NACC (0.8% in PBS/Tween) are shown in FIG. 20. The NACC had no effect on PROM antigen levels in 50 amniotic fluids and 50 normal vaginal fluid specimens, showing that it did not inhibit the immunoreactivity of the PROM antigen. It was, however, active in lysing mucus as observed by visual inspection, and enabled the detection of PROM antigen in 20 vaginal fluid specimens which had given negative results without the NACC treatment. These specimens were considered to be clinically positive, having been collected after ARM.

When the five false negative samples were re-tested with the addition of the mucolytic agent NAC, three of the specimens (numbers 2, 17 and 30, Table 6) now registered a positive result. In the remaining two specimens, no clinical reason could be readily proposed to explain the false negative results. It is reasonable to speculate, however, that there was some inhibiting substance such as albumin to the PROM antigen (Table 4). Another possibility is that the specimen obtained from the vagina consisted largely of mucus and little or no liquor, thus producing a negative result. It is interesting to note that one of these (number 4) was also negative when tested for DAO.

Thus, in only two of the 46 patients (4.3%) was the test result at variance with the expected result (assay specificity of 100%, sensitivity of 94%).

Monoclonal antibody 1A3 referred to herein has been deposited at the European Collection of Animal Cell Cultures (ECACC) and has been allocated accession number 94031901.

TABLE 1

Typical total protein results at different stages of purification of amniotic fluid protein from five random term amniotic fluid.

| Fraction | Volume (mL) | Protein (mg/mL) | Total Protein (mg) | Total Activ. (U) | Specific Activity (U/mg) | Yield (%) | Purification |
|---|---|---|---|---|---|---|---|
| Amniotic Fluid | 10.0 | 5.42 | 54.2 | 960 | 17.7 | 100 | 1 |
| Ammon. sulphate pellet | 5.1 | 7.23 | 36.8 | 840 | 22.8 | 87.5 | 1.28 |
| Post DEAE-Affi Gel Blue | 50.0 | 0.028 | 1.4 | 780 | 557.0 | 81.2 | 31.4 |
| Post Sephacs-200 | 18.0 | 0.02 | 0.36 | 849 | 2080.0 | 78.4 | 117 |

TABLE 2

Reactivity of sera from six immunized mice collected at 15 weeks to human amniotic fluid and human serum.

| | Absorbance at 405 nm* | |
|---|---|---|
| Immunized mouse no. | Amniotic Fluid | Maternal Serum |
| 1 | 0.130 (0.004) | 0.139 (0.004) |
| 2 | 0.349 (0.004) | 0.132 (0.006) |
| 3 | 0.136 (0.003) | 0.126 (0.003) |
| 4 | 0.305 (0.002) | 0.140 (0.004) |
| 5 | 0.203 (0.002) | 0.121 (0.003) |
| 6 | 0.802 (0.006) | 0.141 (0.002) |
| Non-immune mouse sera | 0.136 (0.003) | 0.143 (0.003) |

TABLE 3

Examination of R-Z ratios of the IgG-HRPO conjugate eluted after passage through a BioGel A-0.5 m column.

| Fraction No. | A-403 | A-280 | A-403/A-280* |
|---|---|---|---|
| 1 | 0.0 | 0.001 | — |
| 2 | 0.0 | 0.0013 | — |
| 3 | 0.012 | 0.0688 | 0.17 |
| 4 | 0.046 | 0.127 | 0.27[b] |
| 5 | 0.169 | 0.134 | 0.39[b] |
| 6 | 0.126 | 0.262 | 0.48[b] |
| 7 | 0.063 | 0.084 | 0.34[b] |
| 8 | 0.041 | 0.145 | 0.28[b] |
| 9 | 0.003 | 0.062 | 0.05 |

TABLE 4

Effect of potential interfering substances on PROM-Ag activity.

| Intefering Substances | Mean (U/L) | Range (U/L) |
|---|---|---|
| Amniotic fluid (Control) | 18 | 15–21 |
| Haemolysed serum | 10 | 6–12 |
| Haemolysed serum (-Albumin) | 16 | 14–21 |
| Urine | 18 | 16–20 |
| Tap water | 17 | 15–20 |
| Prostaglandin E2 cream | 18 | 16–21 |
| Cord blood | 11 | 7–14 |
| Cord blood (-Albumin) | 16 | 13–19 |

TABLE 5

Blind study A.

| Patient Number | Pre-CS-PROM Antigen Level (U/L) | Post-CS-ROM PROM Antigen Level (U/L) | Comment |
|---|---|---|---|
| 1 | <10 | | Pre-CS for Triplets |
| 2 | | 60 | Triplet 1 |
| 3 | | 211 | Triplet 2 |
| 4 | | 170 | Triplet 3 |
| 5 | <10 | | |
| 6 | | 60 | |
| 7 | <10 | | Pre-CS for Triplets |
| 8 | | 390 | Triplet 1 |
| 9 | | 321 | Triplet 2 |
| 10 | | 267 | Triplet 3 |
| 11 | <10 | | |
| 12 | | 171 | |
| 13 | <10 | | |
| 14 | | 140 | |
| 15 | <10 | | |
| 16 | | 331 | |

TABLE 6

Blind study B.

| Patient Number | Pre-ARM PROM Antigen Level (U/L) | | | Post-ARM PROM Antigen Level (U/L) | | | Comment |
|---|---|---|---|---|---|---|---|
| | −NAC | +NAC | DOA | −NAC | +NAC | DAO | |
| 1 | <10 | | | 16 | | | |
| 2 | <10 | <10 | <25 | 5 | 11 | 43 | Blood/Muc |
| 3 | <10 | | | 20 | | | |
| 4 | <10 | <10 | <25 | 0 | <10 | <25 | Not ruptured |
| 5 | <10 | | | 18 | | | |
| 6 | 16 | 14 | <25 | 27 | 30 | 585 | Small leak pre-ARM |
| 7 | <10 | <10 | | 39 | 34 | 337 | |
| 8 | <10 | <10 | | 40 | 29 | 85 | Blood/Muc |
| 9 | <10 | | | 16 | | | |
| 10 | <10 | | | 82 | 71 | 158 | Blood |
| 11 | <10 | <10 | | <10 | <10 | 414 | False neg.? Protein/Mec |
| 12 | <10 | <10 | | 18 | 22 | 290 | |
| 13 | | <10 | <25 | | 32 | 384 | |
| 14 | | <10 | <25 | | 19 | 92 | |
| 15 | <10 | | | | | | |
| 16 | <10 | | | | | | |
| 17 | <10 | | | | | | Candida |
| 18 | | | | <10 | 17 | 184 | Mucus effect |
| 19 | | | | 12 | | | |
| 20 | <10 | | | | | | |
| 21 | | | | 15 | | | Blood |
| 22 | <10 | | | | | | |
| 23 | | | | 43 | | | |
| 24 | <10 | | | | | | |
| 25 | 15 | 23 | 40 | | | | Small leak pre-ARM. + DAO |
| 26 | | | | 35 | | 33 | |
| 27 | | | | 24 | | | Blood/Mec |
| 28 | | | | 17 | | | Blood |
| 29 | | | | 12 | | | Blood |
| 30 | | | | <10 | 37 | | Mucus |
| 31 | | | | 22 | | | |
| 32 | | | | | 29 | 280 | |

LEGENDS

TABLE 2 a. Absorbance (405 nm) was measured in a one-site indirect ELISA assay.

b. Mean (SEM) of replicates

TABLE 3 a. R-Z ratio b. Fractions 4–8 of the conjugate were pooled, the R-Z value of the pool was 0.38; the conjugate was stored at 4° C. in 0.1% thimerosal.

FIG. 1

Amniotic fluid proteins following denaturation with SDS/imercaptoethanol during purification of PROM antigen (see arrows) on 4–15% SDS-PAGE gradient gels.

Lanes 1, 2 and 8: Molecular weight standards [(BIORAD) Arrowheads]: 106,000, 80,000, 49,500, 32,500, 27,500, 18,500 Da (top to bottom).

3 Amniotic fluid.

4 Ammonium sulphate pellet of amniotic fluid.

5 Concentrated eluate from DEAE Affi-Gel Blue column.

6, 7 Ammonium sulphate pellets from two maternal sera.

9 Molecular weight standards (Pharmacia: 94,000 (missing), 67,000, 43,000, 30,000, 20,000, 14,400 Da (top to bottom)

FIG. 2

Amniotic fluid proteins following denaturation with SDS/mercaptoethanol during purification of PROM antigen (see arrows) on 4–15% SDS-PAGE gradient gels.

Lanes 1, 6 and 8: Molecular weight standards [(BIORAD) Arrowheads]): 106,000, 80,000, 49,500, 32,500, 27,500, 18,500 Da (top to bottom).

2 Eluate from Sephacryl S-200 Column used for immunization.

3, 7 Eluate from Sephacryl S-200 column.

4, 5 Maternal serum supernatant following ammonium sulphate precipitation.

FIG. 3
Reactivity of hybridoma supernatants with maternal serum and amniotic fluid by indirect on-site ELISA.

FIG. 4
Isolation of monoclonal immunoglobulin from ascitic fluid on a hydroxylapatite column with a 50–500 mM linear gradient of sodium phosphate buffer (pH 7.0).

☐ Absorbance of eluate at 280 nm

■ Absorbance of eluate at 405 nm in a one-site indirect ELISA using human amniotic fluid as capture antigen.

FIG. 5
Agarose gel electrophoresis of monoclonal antibody following hydroxylapatite chromatography Lanes 2 and 7: Two random term amniotic fluids.

3–6 Purified IgG fractions from hydroxylapatite column. Fractions correspond to fractions 30–33 as shown in FIG. 4.

FIG. 6A
Estimation of sub-unit molecular weight of PROM antigen by Western blot analysis with monoclonal 1A3-HRPO conjugate. Electrophoresis, following incubation with SDS/mercaptoethanol was performed on a 4–15% SDS-PAGE gradient gel.

Lanes 1, 5, 6 and 8: Prestained low range molecular weight standards (BIORAD): 106,000, 80,000, 49,500, 32,500, 27,500, 18,500 Da (top to bottom).

2, 3, 4 and 7: Four random amniotic fluids purified by Sephacryl S-200 column chromatography.

FIG. 6B
Standard curve constructed from FIG. 6A.

☐ Molecular weight standards.

■ Position of PROM antigen (55,000+2,000 daltons).

FIG. 7A
Estimation of isoelectric point of PROM antigen by western blot analysis with 1A3-HRPO conjugate. Isoelectric focusing was performed on an agarose gel pH range 3–10.

Lane 1: IEF standards (BIORAD) stained for protein: pI's are 4.65, 5.10, 6.0, 7.0, 7., 7.5, 7.8, 8.0, 8.2 and 9.6 (top to bottom).

2 Purified PROM antigen stained with 1A3-HRPO conjugate.

3 A random term amniotic fluid blotted and stained for protein.

FIG. 7B
Standard curve constructed from FIG. 7A.

☐ Isoelectric focusing pI markers (BIORAD).

■ Position of PROM antigen (pI=4.9).

FIG. 8A
Elution profile of post DEAE Affigel Blue fractions of amniotic fluid from a Sephocryl S-200 column.

☐ Elution profile of standards
(I) thyroglobulin 670,000 Da,
(II) bovine gamme globulin 158,000 Da,
(III) chicken ovalbumin (44,000 Da),
(IV) equine myoglobin (17,500 Da), and
(V) vitamin B12 (1350 Da).

■ Protein elution profile (absorbance at 280 nm).

FIG. 8B
Estimation of the native molecular weight of PROM antigen by gel permeation chromatography on a Sephacryl S-200 column.

☐ Elution profile of standards (absorbance at 280 nm).

■ Elution profile of PROM antigen as determined by indirect one-site ELISA screening.

FIG. 8C
Estimation of the native molecular weight of PROM antigen from molecular weight standards passed through a column of Sephacryl S-200.

Elution profile of gel permeation standards: (I) 670,000, (II) 158,000, (III) 44,000, (IV) 17,500 and (V) 1,350 daltons (absorbance at 280 nm).

○ Standard curve (Log MW of gel permeation standards [BIORAD]).

■ Position of PROM antigen (Native Mw=330,000 daltons).

FIG. 9
Effect of varying capture antibody concentration used on coating wells in the detection of three amniotic fluids and three maternal sera.

☐ Mean (SD) of three amniotic fluids.

■ Mean (SD) of three maternal sera.

FIG. 10
Effect of four different blocking agents on the reactivity of serial dilutions of PROM antigen in an amniotic fluid pool.

☐ 100 mM lysine, 0.5% BSA (w/v) in 100 mM sodium phosphate buffer pH 8.0.

PBS, 5% (w/v) milk powder.

○ 100 mM lysine in 100 mM sodium phosphate pH 8.0.

PBS, 1% (v/v) swine serum.

FIG. 11
Effect of dilution of the 1A3-HRPO conjugate on the reactivity of five random amniotic fluids.

☐ Mean (SD) of five random term amniotic fluids.

FIG. 12
Effect of three different sample diluents upon the reactivity of an amniotic fluid pool.

☐ PBS/Tween.

■ PBS

○ PBS/Swine serum.

FIG. 13
Effect of sample diluent pH on the reactivity of serial dilutions of an amniotic pool.

FIG. 14
Effect of varying sample incubation time on the reactivity of three amniotic fluids.

☐ Mean.

FIG. 15
Effect of varying incubation time with 1A3-HRPO conjugate on reactivity on an amniotic fluid pool.

☐ Mean (SD) of three random amniotic fluids.

FIG. 16
Effect of varying incubation time with HRPO substrate on the reactivity of different dilutions of an amniotic fluid pool.

FIG. 17
Typical standard curve obtained with the optimized ELISA procedure.

Mean (SD) of standards in five different runs.

FIG. 18
Dilution of three individual term amniotic fluids compared with the standard curve.

■ Standard amniotic fluid pool.

+×● Individual amniotic fluids.

FIG. 19
Precision profile of 120 vaginal fluid specimens. CV is calculated from duplicates as the difference×100/mean.

FIG. 20
Effect of pre-incubation with N-Acetyl cysteine on PROM antigen levels in 40 amniotic fluids.

A.F. Amniotic Fluid
N-ACC N-Acetylcysteine
V.F. Vaginal Fluid
FIG. 21
Reference range of PROM antigen levels in 1st, 2nd and 3rd trimester amniotic fluid.

We claim:

1. An antigen located in amniotic fluid characterised by possessing the following physical properties:
   (i) a sub-unit molecular weight of approximately 55,000 daltons performed by SDS-PAGE with gels of different acrylamide concentrations;
   (ii) a native molecular weight analysis as determined by gel permeation chromatography revealing an apparent molecular weight of approximately 330,000 daltons.
   (iii) a band observed having an isolectric point of approximately 4.9 revealed by isoelectric focussing studies; and
   (iv) immunoreactive with a monoclonal antibody 1A3 deposited at the European Animal Cell Culture Collection and having Accession No. 94V31901.

2. A method of purification of the antigen according to claim 1, from amniotic fluid including the steps of:
   (i) reaction of amniotic fluid with ammonium sulphate;
   (ii) centrifuging the product of reaction (i) and obtaining the resulting pellet or precipitate;
   (iii) resuspending the pellet or precipitate in buffer and passing the resulting solution through a column of DEAE Affi-Gel Blue;
   (iv) testing unbound fractions after passage through the column for the presence of a protein of sub-unit molecular weight of approximately 55,000 daltons by SDS-PAGE electrophoresis.
   (v) concentrating fractions having said molecular weight of 55,000 daltons and passing said concentrated fractions through a Sephacryl S-200 column and collecting fractions with a molecular weight of 330,000.

3. A method as claimed in claim 2 wherein the buffer is 0.02M $K_2HPO_4$.

4. A binding agent immunoreactive with the antigen of claim 1.

5. A binding agent as claimed in claim 4 wherein said binding agent is a monoclonal or polyclonal antibody.

6. Monoclonal antibody 1A3 deposited at the European Animal Cell Culture Collection and having accession number 94031901.

7. A method of detection of rupture of the amniotic membrane in pregnant mammals including humans including the steps of:
   (i) obtaining a sample of vaginal fluid from a pregnant female;
   (ii) reacting the sample with antibody derived from an antigen characterized by possessing the following physical properties:
      (a) a sub-unit molecular weight of approximately 55,000 daltons performed by SDS-PAGE with gels of different acrylamide concentrations;
      (b) a native molecular weight analysis as determined by gel permeation chromatography revealing an apparent molecular weight of approximately 330,000 daltons
      (c) a band observed having an isoelectric point of approximately 4.9 revealed by isolectric focussing studies; and
      (d) immunoreactive with a monoclonal antibody 1A3 deposited at the European Animal Cell Culture Collection and having Accession No. 94V31901; and
   (iii) detecting reactivity in step by means of an immunoassay (ii).

8. A method of detection as claimed in claim 7 wherein the antibody is monoclonal antibody 1A3.

9. A method of detection as claimed in claim 7 wherein the antibody is immobilized to an inert surface.

10. A method as claimed in claim 7 wherein the antibody has an enzyme attached thereto which is reactive with an enzyme substrate thereby providing signal amplification of the immunoassay.

11. A method as claimed in claim 10 wherein the enzyme is horse radish peroxidase.

12. A method as claimed in claim 10 wherein the enzyme subtrate is azinobis (3-ethylbenztniazoline sulphric acid) diamnonium salt.

* * * * *